US012427229B2

(12) United States Patent
Zergioti et al.

(10) Patent No.: US 12,427,229 B2
(45) Date of Patent: Sep. 30, 2025

(54) LASER ABLATION/REMOVAL AND LASER INDUCED FORWARD TRANSFER OF BIOLOGICAL MATERIAL

(71) Applicant: PhosPrint P.C., Athens (GR)

(72) Inventors: Ioanna Zergioti, Athens (GR); Apostolos Klinakis, Athens (GR)

(73) Assignee: PhosPrint P.C., Athens (GR)

( * ) Notice: Subject to any disclaimer, the term of this patent is extended or adjusted under 35 U.S.C. 154(b) by 1080 days.

(21) Appl. No.: 17/387,801

(22) Filed: Jul. 28, 2021

(65) Prior Publication Data

US 2022/0040377 A1 Feb. 10, 2022

Related U.S. Application Data

(60) Provisional application No. 63/062,176, filed on Aug. 6, 2020.

(51) Int. Cl.
*B33Y 10/00* (2015.01)
*A61B 18/20* (2006.01)
(Continued)

(52) U.S. Cl.
CPC .......... *A61L 27/3691* (2013.01); *A61B 18/20* (2013.01); *A61L 27/28* (2013.01);
(Continued)

(58) Field of Classification Search
CPC ............................... B33Y 10/00; C12M 33/00
See application file for complete search history.

(56) References Cited

U.S. PATENT DOCUMENTS 6,905,738 B2   6/2005   Ringeisen et al.
6,936,311 B2   8/2005   Ringeisen et al.
(Continued)

FOREIGN PATENT DOCUMENTS

AU   2002243924 A1   9/2002
CZ   1641955          3/2012
(Continued)

OTHER PUBLICATIONS

Serrano-Aroca et al. Bioengineering Approaches for Bladder Regeneration. International Journal of Molecular Sciences. Vo. 19. 1796. 2018 (Year: 2018).*
(Continued)

*Primary Examiner* — Cachet I Proctor
(74) *Attorney, Agent, or Firm* — Suiter Swartz IP

(57) ABSTRACT

A method for cell printing is disclosed. The method includes generating a receiver substrate, ablating or removing a portion of the receiver substrate via a first laser to expose a target layer, generating a donor substrate containing a back surface and a front surface, applying a coating of donor material to the front surface. The method further includes aligning the front surface of the donor substrate to be parallel to and facing the receiver substrate, wherein the donor material is disposed adjacent to the target layer, and irradiating the coating through the back surface of the donor substrate with one or more laser pulses produced by a second laser to transfer a portion of the donor material to the target layer. A system for cell printing is also disclosed.

11 Claims, 19 Drawing Sheets

(51) Int. Cl.
*A61L 27/28* (2006.01)
*A61L 27/36* (2006.01)
*B41M 3/00* (2006.01)
*A61B 17/00* (2006.01)
*A61B 18/00* (2006.01)

(52) U.S. Cl.
CPC ....... *A61L 27/3604* (2013.01); *A61L 27/3679* (2013.01); *B41M 3/006* (2013.01); *A61B 2017/00969* (2013.01); *A61B 2018/00494* (2013.01); *A61B 2018/00505* (2013.01); *A61B 2018/00577* (2013.01)

(56) References Cited

U.S. PATENT DOCUMENTS

| | | |
|---|---|---|
| 7,001,467 B2 | 2/2006 | Piquéet al. |
| 7,507,422 B2 | 3/2009 | Kropp et al. |
| 7,875,324 B2 | 1/2011 | Barron et al. |
| 9,039,998 B2 * | 5/2015 | Guillemot ............ C12M 33/04 422/509 |
| 9,328,327 B2 | 5/2016 | Haverich |
| 9,629,989 B2 | 4/2017 | Guillemot et al. |
| 9,855,369 B2 | 1/2018 | Murphy et al. |
| 10,112,388 B2 | 10/2018 | Guillemot |
| 10,196,596 B2 | 2/2019 | Glazier et al. |
| 2009/0246247 A1 | 10/2009 | Shetty et al. |
| 2011/0250688 A1 | 10/2011 | Hasan |
| 2011/0313429 A1* | 12/2011 | Anderson .......... A61B 10/0233 606/131 |
| 2015/0351896 A1 | 12/2015 | D'Lima et al. |
| 2016/0243286 A1 | 8/2016 | Collins et al. |
| 2016/0257926 A1 | 9/2016 | Rivron et al. |
| 2017/0196674 A1 | 7/2017 | Abdel-Meguid et al. |
| 2017/0320263 A1 | 11/2017 | Guillemot |
| 2017/0360551 A1 | 12/2017 | Liu |
| 2019/0328935 A1 | 10/2019 | Kang et al. |
| 2020/0055327 A1 | 2/2020 | Batt |
| 2020/0080060 A1 | 3/2020 | Matheu et al. |
| 2020/0102529 A1 | 4/2020 | Guillemot et al. |

FOREIGN PATENT DOCUMENTS

| | | |
|---|---|---|
| EP | 2542659 B1 | 3/2018 |
| EP | 3234102 B1 | 6/2018 |
| EP | 3526007 A1 | 8/2019 |
| FR | 3063930 B1 | 3/2019 |
| RU | 2323688 C1 | 5/2008 |
| RU | 2371102 C1 | 10/2009 |
| RU | 2408305 C1 | 1/2011 |
| UA | 53768 C2 | 2/2003 |
| UA | 55215 A | 3/2003 |
| WO | 2016124708 A1 | 8/2016 |
| WO | 2017187114 A1 | 11/2017 |
| WO | 2018193446 A1 | 10/2018 |
| WO | 2018193454 A1 | 10/2018 |
| WO | 2019060518 A1 | 3/2019 |
| WO | 2019122351 A1 | 6/2019 |
| WO | WO-2019129349 A1 * | 7/2019 ............ B23K 26/00 |
| WO | 2019198086 A1 | 10/2019 |

OTHER PUBLICATIONS

Fraser, M. et al., (2004), "A surgical model of composite cystoplasty with cultured urothelial cells: a controlled study of gross outcome and urothelial phenotype", BJU International, 93: 609-616. doi:10.1111/j.1464-410X.2003.04675.x, 9 pages.

Jonason et al., Manuscript, "Primary Murine Growth Plate and Articular Chondrocyte Isolation and Cell Culture" published in Osteoporosis and Osteoarthritis on Sep. 17, 2014, 8 pages.

Kalabis et al., Manuscript, "Isolation and characterization of mouse and human esophageal epithelial cells in 3D organotypic culture" published in Nature Protocols, on Jan. 12, 2012, 12 pages.

Munaz, A. et al., "Three-dimensional printing of biological matters", Journal of Science: Advanced Materials and Devices, 1 (2016) 1-17.

Murphy, S. et al., "3D bioprinting of tissues and organs", Nat Biotechnol 32, 773-785 (2014). https://doi.org/10.1038/nbt.2958.

Nik et al., Manuscript, "Separation of Intact Intestinal Epithelium from Mesenchyme" published in Biotechniques on Jul. 2014, 3 pages.

Oberpenning, F. et al., "De novo reconstitution of a functional mammalian urinary bladder by tissue engineering", Nat Biotechnol 17, Abstract Only (1999). https://doi.org/10.1038/6146.

Precise Bio, URL: https://www.precise-bio.com/, downloaded Apr. 24, 2020, 3 pages.

Prellis Biologics, URL: https://www.prellisbio.com/tech, downloaded Apr. 24, 2020, 1 page.

Oberpenning, F. et al., "De novo reconstitution of a functional mammalian urinary bladder by tissue engineering", Nat Biotechnol 17, (1999). https://doi.org/10.1038/6146.

European Patent Office, International Search Report and Written Opinion for International Application No. PCT/GR2021/000052, Nov. 26, 2021, 18 pages.

Higbee et al., "Femtosecond Laser Ablation of Porcine Intestinal Mucosa: Potential Autologous Transplant for Segmental Cystectomy," Proceedings of SPIE, vol. 5686, Photonic Therapeutics and Diagnostics, Apr. 25, 2005, 12 pages.

Koo et al., "Laser-assisted Biofabrication in Tissue Engineering and Regenerative Medicine," JMR Early Career Scholars in Materials Science Annual Issue: Review, vol. 32, No. 1, Dec. 19, 2016, 15 pages.

Pere Serra et al., "Laser-Induced Forward Transfer: Fundamentals and Applications," Advanced Materials Technologies, vol. 4, No. 1, Aug. 8, 2018, 33 pages.

Serrano-Aroca et al., "Bioengineering Approaches for Bladder Regeneration," International Journal of Molecular Sciences, vol. 19, No. 6, Jun. 17, 2018, 26 pages.

* cited by examiner

LASER ABLATION/REMOVAL AND LASER INDUCED FORWARD TRANSFER OF BIOLOGICAL MATERIAL

PRIORITY

The present application claims the benefit under 35 U.S.C. § 119(e) of U.S. Provisional App. No. 63/062,176 filed by Zergioti on Aug. 6, 2020 entitled "LASER ABLATION/REMOVAL AND LASER INDUCED FORWARD TRANSFER OF BIOLOGICAL MATERIAL", which is incorporated herein by reference in its entirety.

TECHNICAL FIELD

The present invention generally relates to the fields of cell biology and tissue engineering, and, more particularly, to a system and method of modifying and generating biological tissues for transplantation.

BACKGROUND

Tissue engineering is the science of using cells and other supporting material to generate and grow tissues and organs, often for use in transplantation. Cells from donor tissues may be isolated and repositioned on an artificial or biological substrate. The newly formed tissue may then be transplanted into the body. Tissue engineering requires considerable skill to ensure that the building of cells and supporting material upon the substrate is performed competently. Biological substrates, such as intestinal tissue derived from a transplant recipient, are often utilized in tissue engineering procedures as they are autologous and thus tolerated by the immune system. However, the use of intestinal tissue as a substrate for a non-intestinal tissue-engineered transplant, such as urinary bladder can be problematic due to the absorptive and secretive nature of intestinal tissue. Thus, it is desirable to provide a method and product that avoids the shortcomings of conventional approaches.

SUMMARY

A method is disclosed. In some embodiments, the method includes generating a receiver substrate. In some embodiments, the method further includes at least one of ablating or removing a portion of the receiver substrate via a first laser to expose a target layer of the receiver substrate. In some embodiments, the method further includes generating a donor substrate. In some embodiments, the donor substrate comprises a back surface and a front surface. In some embodiments, the method further includes applying a coating to the front surface. In some embodiments, the coating includes donor material. In some embodiments, the method further includes aligning the front surface of the donor substrate to be parallel to and facing the receiver substrate. In some embodiments, the donor material is disposed adjacent to the target layer: in some embodiments, the method further includes irradiating the coating through the back surface of the donor substrate with one or more laser pulses produced by a second laser to transfer a portion of the donor material to the target layer.

In one or more embodiments, the method further includes scanning the donor substrate through a focal point of the second laser while irradiating the donor material with the second laser to continuously provide new donor material to transfer to the receiver substrate. In one or more embodiments, the method further includes scanning the receiver substrate while irradiating the donor material with the second laser to form a selected pattern of the donor material on the target layer.

In one or more embodiments of the method, the selected pattern of the donor material on the target layer includes a layer of the donor material on the target layer In one or more embodiments of the method, the receiver substrate includes intestinal tissue. In one or more embodiments, the donor material includes urothelial cells.

In one or more embodiments of the method, ablating a portion of the receiver substrate via the first laser to expose the target layer of the receiver substrate includes ablating one or more crypt cells from the intestinal tissue.

In one or more embodiments of the method, ablating a portion of the receiver substrate via the first laser to expose the target layer of the receiver substrate includes denuding at least a portion of an epithelial layer of the intestinal tissue In one or more embodiments of the method, the urothelial cells include at least one of differentiated induced pluripotent stem cells (iPS) or stem cells of mesodermal or endodermal origin.

In one or more embodiments of the method, the urothelial cells are derived from donors other than the receiver substrate.

In one or more embodiments of the method, the donor material includes at least one of a tissue, a protein, a nucleic acid, an extracellular material, a scaffolding material, an epithelial cell, a urothelial cell, a fibroblast, a mesenchymal cell, an adipocyte, an immune cell, a muscle cell, a nerve cell, an insulinogenic cell, a keratinocyte, a chondrocyte or a stem cell.

In one or more embodiments of the method, the receiver substrate includes at least one of an extracellular matrix, intestinal tissue, bladder tissue, stomach tissue, cartilaginous tissue, esophageal tissue, a cell-containing tissue, an organ, a portion of an organ, or an organoid.

In one or more embodiments of the method, the applying the coating includes applying a dynamic release layer to the front surface of the donor substrate. In one or more embodiments of the method, the applying the coating includes applying the donor material to the dynamic release layer.

In one or more embodiments of the method, the at least one of ablating or removing removes at least one of a cell, an intestinal crypt, an extracellular matrix, a tissue, or portion of an organ from the receiver substrate.

In one or more embodiments of the method, the method further includes treating the receiving substrate by at least one of mechanical or enzymatic means.

A system is disclosed. In some embodiments, the system includes a first laser configured to generate a first laser beam. In some embodiments, the system further includes a second laser configured to generate a second laser beam. In some embodiments, the system further includes one or more optical elements configured to direct the first laser beam and the second laser beam through a focusing lens. In one or more embodiments, the system further includes one or more beam control elements configured to selectively transmit a selected combination of first laser beam or the second laser beam through the focusing lens. In one or more embodiments, the system further includes a first translation stage assembly adapted to support a donor substrate. In some embodiments, the donor substrate includes a back surface. In some embodiments, the donor substrate further includes a front surface. In some embodiments, the donor substrate further includes a coating disposed on the front surface. In some embodiments, the coating includes a donor material. In some embodiments, the system further includes a second translation stage assembly adapted to support a receiver substrate. In some embodiments, the system further includes a controller communicatively coupled to the first and second translation stage assemblies and the one or more beam control elements. In some embodiments, the controller is configured to direct the second translation stage assembly to align the receiver substrate to a focal plane of the objective lens. In some embodiments, the controller is configured to direct at least one of the second translation stage assembly or the one or more beam control elements to at least one or ablate or remove a portion of the receiver substrate to expose a target layer of the receiver substrate. In some embodiments, the controller is configured to direct at least one of the first translation stage or the second translation stage to align the front surface of the donor substrate to be parallel to and facing the receiver substrate. In some embodiments, the coating on the donor substrate is located at the focal plane of the objective lens. In some embodiments, the controller is configured to direct at least one of first translation stage, the second translation stage, or the one or more beam control elements to irradiate the coating through the back surface of the donor substrate to transfer a portion of the donor material to the target layer of the receiver substrate.

In one or more embodiments of the system, the directing at least one of the first translation stage, the second translation stage, or the one or more beam control elements to irradiate the coating through the back surface of the donor substrate to transfer a portion of the donor material to the target layer of the receiver substrate includes directing at least one of the first translation stage, the second translation stage, or the one or more beam control elements to scan the donor substrate through a focal point of the second laser while irradiating the donor material with the second laser to continuously provide new donor material to transfer to the receiver substrate. In one or more embodiments of the system. In one or more embodiments, directing at least one of the first translation stage, the second translation stage, or the one or more beam control elements to irradiate the coating through the back surface of the donor substrate to transfer a portion of the donor material to the target layer of the receiver substrate further includes directing at least one of first translation stage, the second translation stage, or the one or more beam control elements to scan the receiver substrate while irradiating the donor material with the second laser to form a selected pattern of the donor material on the target layer of the receiver substrate.

In one or more embodiments of the system, the selected pattern of the donor material on the target layer includes a layer of the donor material on the target layer.

In one or more embodiments of the system, directing at least one of the second translation stage or the one or more beam control elements to at least one or ablate or remove the portion of the receiver substrate to expose the target layer of the receiver substrate includes directing at least one of the second translation stage or the one or more beam control elements to remove at least one of a cell, an intestinal crypt, an extracellular matrix, or a tissue from the receiver substrate to expose the target layer of the receiver substrate.

In one or more embodiments of the system, the receiver substrate comprises at least one of a tissue, an organ, a portion of an organ, or an organoid.

In one or more embodiments of the system, the tissue comprises at least one of intestinal tissue bladder tissue, stomach tissue, cartilaginous tissue, or esophageal tissue.

Another method is disclosed. In some embodiments, the method includes generating a receiver substrate. In some embodiments, the method further includes at least one of ablating or removing a portion of the receiver substrate to expose a target layer of the receiver substrate. In some embodiments, the method further includes generating a donor substrate. In some embodiments, the donor substrate comprises a back surface and a front surface. In some embodiments, the method further includes applying a coating to the front surface, in some embodiments, the coating includes donor material. In some embodiments, the method further includes aligning the front surface of the donor substrate to be parallel to and facing the receiver substrate. In some embodiments, the donor material is disposed adjacent to the target layer; in some embodiments, the method further includes irradiating the coating through the back surface of the donor substrate with one or more laser pulses produced by a second laser to transfer a portion of the donor material to the target layer. In some embodiments, the method further includes scanning the donor substrate through a focal point of the second laser while irradiating the donor material with the second laser to continuously provide new donor material to transfer to the receiver substrate. In some embodiments, the method further includes scanning the receiver substrate while irradiating the donor material with the second laser to form a selected pattern of the donor material on the target layer.

In one or more embodiments of the method, the receiver substrate comprises at least one of an extracellular matrix, intestinal tissue, bladder tissue, stomach tissue, cartilaginous tissue, esophageal tissue, a cell-containing tissue, an organ, a portion of an organ, or an organoid.

In one or more embodiments of the method, the donor material comprises at least one of a tissue, a protein, a nucleic acid, an extracellular material, a scaffolding material, an epithelial cell, a urothelial cell, a fibroblast, a mesenchymal cell, an adipocyte, an immune cell, a muscle cell, a nerve cell, an insulinogenic cell, a keratinocyte, a chondrocyte or a stem cell.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to a system and method for engineering a transplantable tissue through a preparation of a biological substrate and the building of cells upon the biological substrate. In embodiments, the preparation of the biological substrate involves the use of an ablation/removal laser to remove cells and other organic material from the biological substrate. Laser ablation/removal can be also combined with enzymatic or mechanical pretreatment of the biological substrate. Cells and/or other biological components are then deposited upon the prepared biological substrate by means of a laser equipped with laser induced forward transfer (LIFT) technology. Once the cells and/or other biological material have been deposited on the prepared biological substrate, the engineered tissue may then be prepared for transplantation.

Figure 1:
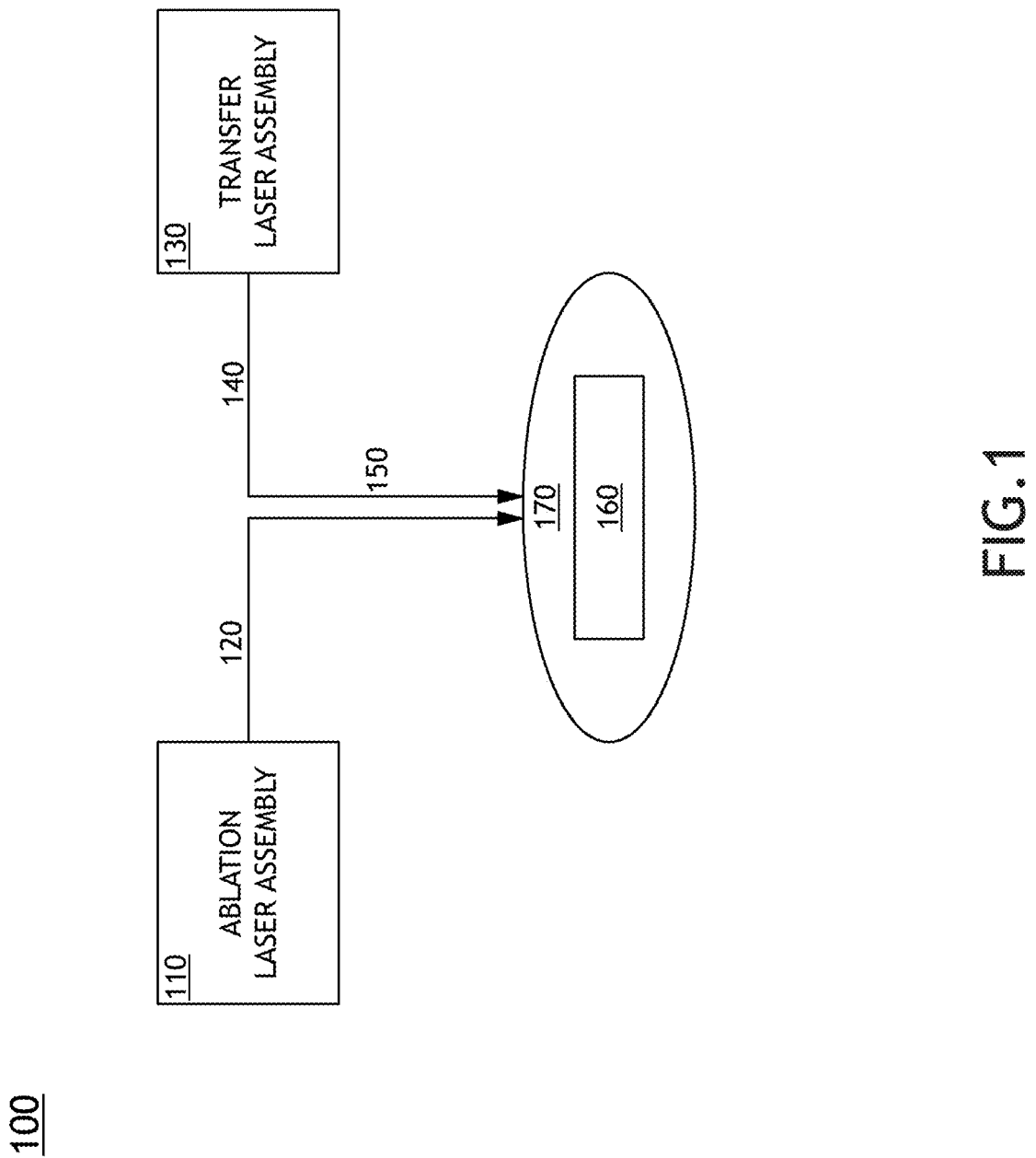
FIG. 1 illustrates a diagram of a system for ablation/removal and transfer of material, in accordance with one or more embodiments of the present disclosure.

FIG. 1 illustrates a diagram of a system 100 for ablation/removal and transfer of material, in accordance with one or more embodiments of the present disclosure. In some embodiments, the system 100 includes an ablation/removal laser assembly 110 that is configured to produce an ablation/removal beam 120. The system 100 further includes a transfer laser assembly 130 configured to produce a transfer beam 140 capable of laser induced forward transfer (LIFT). In embodiments, the ablation/removal beam 120 and the transfer beam 140 are directed through a shared common path 150 to a receiver substrate 160 positioned on a stage 170. In this manner, the system 100 may ablate and/or remove material from and transfer material to a receiver substrate 160 using the shared common path 150.

It should be understood that the terms ablate and remove may both be used to describe the partial or whole removal of biological tissue from a receiver substrate. Ablation is the removal material through an eroding process (e.g., through sublimation or evaporation). Removal is the displacement of material from one location to another. A laser may have ablation capabilities, removal capabilities, or a combination of ablation and removal capabilities.

The receiver substrate 160 may be any tissue, organ, organoid, graft, or other material that may be a substrate for tissue engineering and/or transplantation. For example, the receiver substrate 160 may be a tissue excised from a human patient that will be transplanted back into the patient after modification by the system 100. For instance, the receiver substrate 160 may be intestinal tissue that has been excised from the patient and modified by the system 100, then repurposed as a bladder wall component in order to increase the size and urine holding capacity of the bladder, a technique known as augmentation cystoplasty. In another instance, insulinogenic β-cells may be similarly printed on intestinal smooth muscle, or onto any other splanchnic tissue. In still another instance, colonic cells may be similarly printed on intestinal smooth muscle for large intestine regeneration. Similar techniques may also be used for ureter and urethra engineering. The receiver substrate 160 may be any source of muscle tissue (e.g., smooth muscle tissue) with or without stromal tissue). The receiver substrate 160 may also include other biological tissues including but not limited to smooth muscle tissue, skeletal muscle tissue, blood vessels, skin, bone, connective tissue (e.g., facia), epithelial tissue, and nervous tissue. For example, the receiver substrate may include any section of the gastrointestinal tract (e.g., stomach), the diaphragm, the uterus or fallopian tubes. In another example, the receiver substrate may include bladder tissue, cartilaginous tissue or esophageal tissue.

Figure 2:
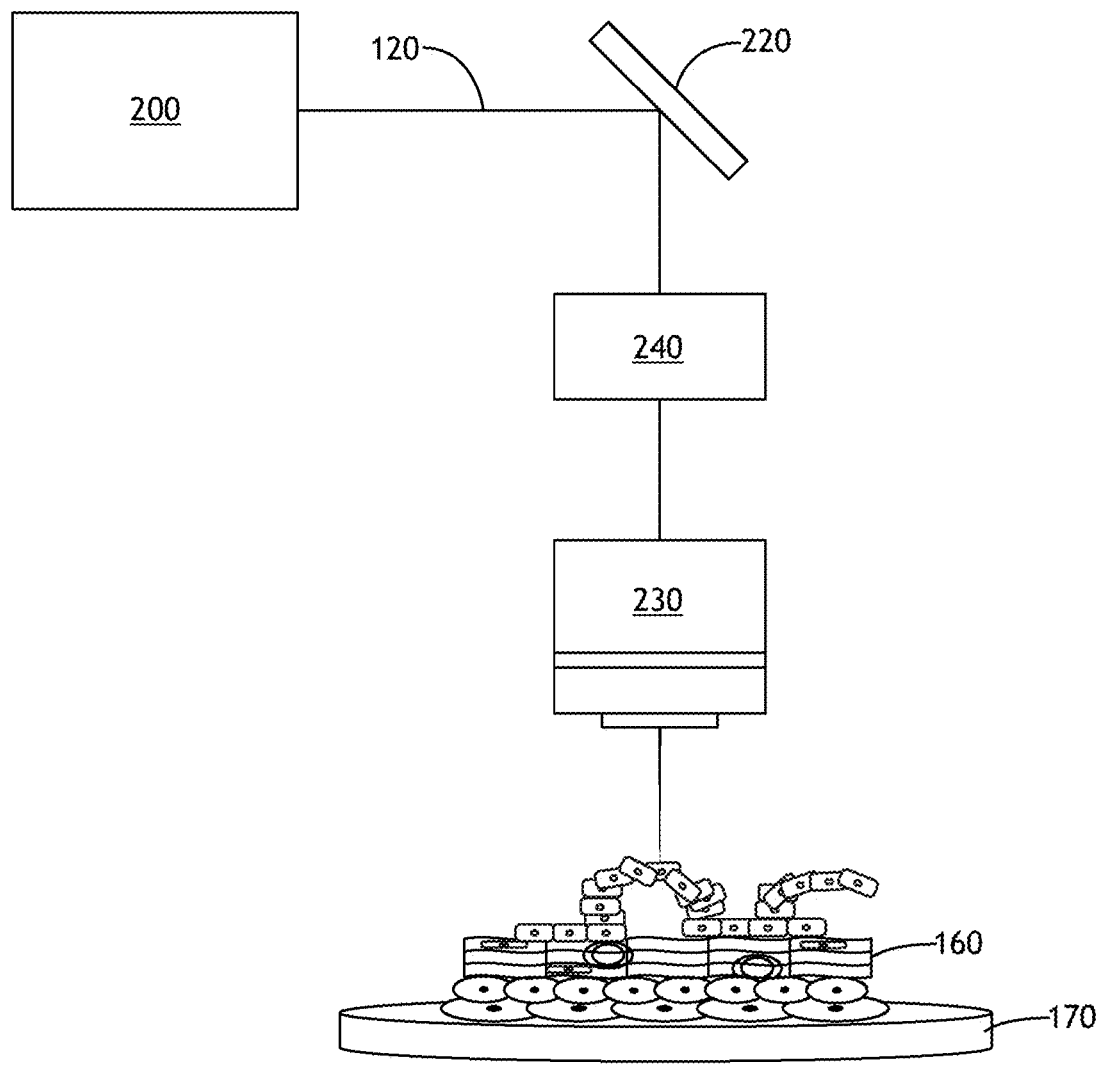
FIG. 2 illustrates a diagram of the ablation/removal laser assembly of the system, in accordance with one or more embodiments of the present disclosure.

FIG. 2 illustrates a diagram of the ablation/removal laser assembly 110 of the system 100, in accordance with one or more embodiments of the present disclosure. In embodiments, the ablation/removal laser assembly 110 includes an ablation/removal laser 200. The ablation/removal laser 200 removes (e.g., denudes) material from the receiver substrate 160 in preparation for deposition of material by the transfer beam 140.

The material removed by the ablation/removal laser 200 may be any cells, cellular material, extracellular tissue (e.g., extracellular matrix), tissue, organ, or portion of an organ. For example, the material removed by the ablation/removal laser 200 may be crypt cells (i.e., intestinal epithelial cells) removed from intestinal tissue. In another example, the material removed by the ablation/removal laser 200 are hyperplasias (e.g., small masses of proliferating cells).

The ablation/removal laser 200 may be any laser known in the art used for ablating material including but not limited to a solid-state laser, a gas laser, a dye laser, or a semiconductor laser. For example, the ablation/removal laser 200 may be a diode-pumped solid-state laser. For instance, the ablation/removal laser 200 may be a diode-pumped Nd:YAG solid-state micro-laser.

The ablation/removal beam 120 produced by the ablation/removal laser 200 may be of any wavelength or wavelength range known in the art. For example, the ablation/removal laser 200 may produce an ablation/removal beam 120 in the visible spectrum (e.g., 380 to 780 nm). In another example, the ablation/removal laser 200 may produce an ablation/removal beam 120 in the near infrared spectrum (e.g., 780 to 2500 nm). For instance, the ablation/removal beam 120 may have a wavelength of approximately 1064 nm.

In some embodiments, the ablation/removal beam 120 produced by the ablation/removal laser 200 may be pulsed. The pulse rate (e.g., repetition rate) of the ablation/removal beam 120 may be any pulse rate or range of pulse rates known in the art. For example, the ablation/removal laser 200 may produce an ablation/removal beam 120 with a pulse rate ranging from 100 Hz to 10 kHz. In another example, the ablation/removal laser 200 may produce an ablation/removal beam 120 with a pulse rate ranging from 300 Hz to 3 kHz. In another example, the ablation/removal laser 200 may produce an ablation/removal beam 120 with a pulse rate of approximately 1 kHz. In another example, the ablation/removal laser 200 may produce a singular pulse.

In embodiments, the ablation/removal laser 200 produces a pulsed ablation/removal beam 120 with a specific pulse length or range of pulse lengths. The pulse length of the ablation/removal beam 120 may be any pulse rate known in the art. For example, the length of the pulse of the ablation/removal beam 120 may range from 60 ps to 6 ns. In another example, the length of the pulse of the ablation/removal beam 120 may range from 100 ps to 30 ns. In another example, the length of the pulse of the ablation/removal beam 120 may be approximately 600 ps.

In embodiments, the ablation/removal laser 200 produces an ablation/removal beam 120 with a specific fluence or range of fluences (e.g., optical energy delivered per unit area). The fluence of the ablation/removal beam 120 may be any range or value known in the art. For example, the fluence of the ablation/removal beam 120 may range from 10 mJ/cm$^2$ to 10 J/cm$^2$. In another example, the fluence of the ablation/removal beam 120 may range from 100 mJ/cm$^2$ to 1 J/cm$^2$. In another example, the fluence of the ablation/removal beam 120 may range from 100 mJ/cm$^2$ to 500 mJ/cm$^2$. In still another example, the fluence of the ablation/removal beam 120 may range from 300 mJ/cm$^2$ to 800 mJ/cm$^2$.

In embodiments, the ablation/removal laser assembly 110 includes one or more optical elements configured to direct the ablation/removal beam 120 to the receiver substrate 160. The optical elements may be any known in the art including but not limited to mirrors, lenses, and beamsplitters. For example, the optical element may include one or more reflecting mirrors 220.

In embodiments, the one or more optical elements includes an focusing lens 230. The focusing lens 230 controls the size of the ablation/removal spot upon the receiver substrate. The focusing lens 230 may be any type of lens known in the art including but not limited to an achromatic lens. For example, the focusing lens 230 may be a 150 mm achromatic lens. In another example, the focusing lens 230 may be a microscope objective.

The size of the ablation/removal spot controlled by the focusing lens 230 may be any size of ablation/removal spot known in the art. For example, the ablation/removal spot may range from 10 um to 1 mm in diameter. In another example, the ablation/removal spot may range from 30 um to 300 um in diameter. In another example, the ablation/removal spot may be approximately 100 um.

In embodiments, the ablation removal laser assembly 110 may include an optical attenuator 240 configured to modify the ablation/removal beam 120. The optical attenuator 240 may be any optical attenuator known in the art including but not limited to a fixed attenuator, a loopback attenuator, an adjustable attenuator, or a variable optical test attenuator. For example, the optical attenuator 240 may be a fixed attenuator plate.

Figure 3:
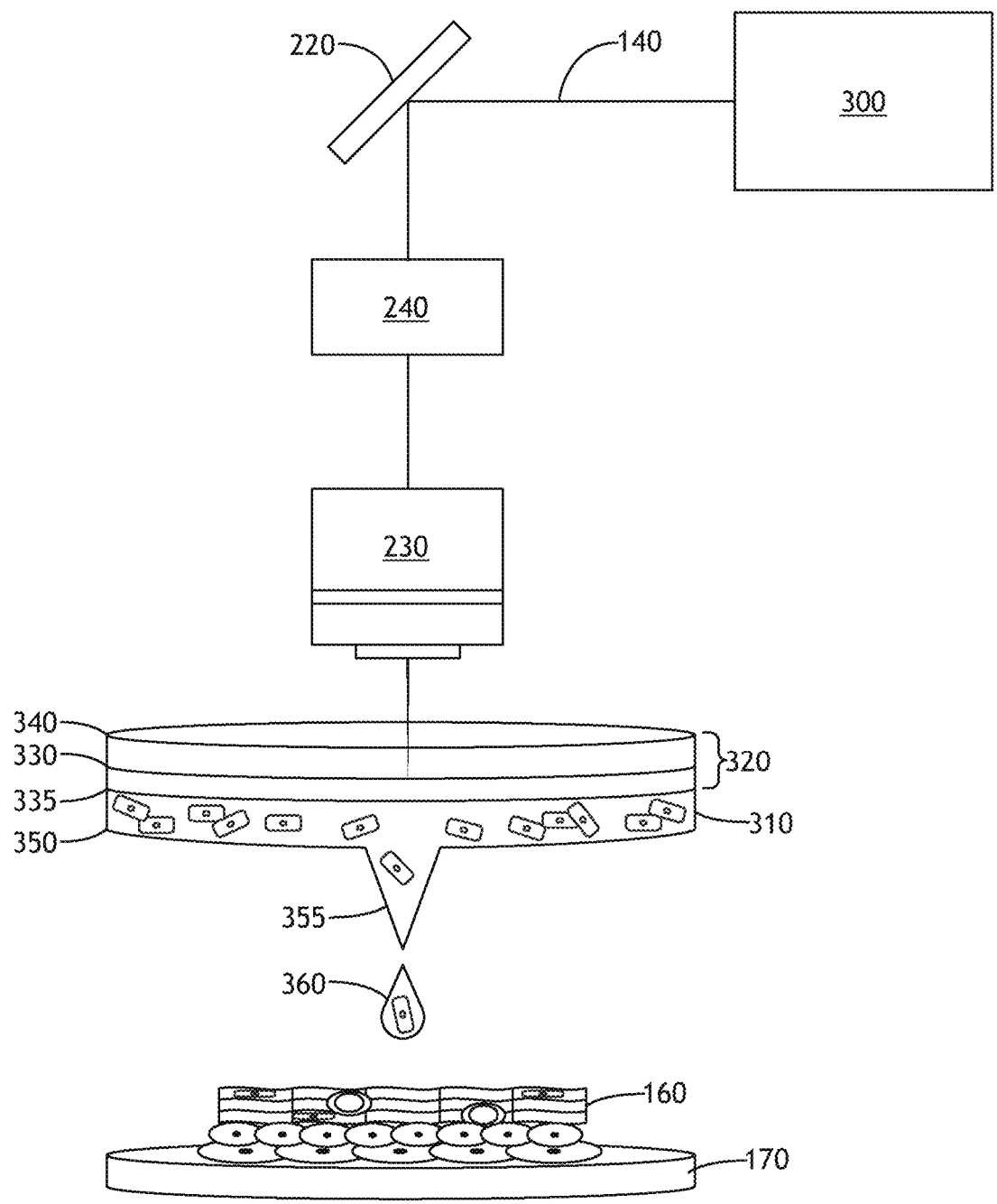
FIG. 3 illustrates a diagram of the transfer laser assembly of the system, in accordance with one or more embodiments of the present disclosure.

FIG. 3 illustrates a diagram of the transfer laser assembly 130 of the system 100, in accordance with one or more embodiments of the present disclosure. In embodiments, the transfer laser assembly 130 includes transfer laser 300. The transfer laser 200 produces a transfer beam 140 that transfers donor material 310 to the receiver substrate 160.

The donor material 310 may be any material that is to be deposited onto the receiver substrate 160, including but not limited to a cell, a tissue, a protein, a nucleic acid, an extracellular material, an intracellular material, or a scaffolding material. For example, the donor material 310 may be a urothelial cell, a fibroblast, a mesenchymal cell, an adipocyte, a keratinocyte (e.g., esophageal keratinocytes), a chondrocyte an immune cell, a muscle cell, a nerve cell, an insulinogenic cell, or a stem cell. For instance, the donor material may be urothelial cells that were harvested from bladder tissue or bladder-like tissues (e.g., urothelial cells scraped from a portion of a bladder, ureter, urethra, or renal pelvis). In another instance, the cell may be an insulinogenic β. In another instance, the cell may be an intestinal epithelial cell.

It should be understood that the donor material 310 may be derived from the recipient of the tissue transplant (e.g., an autologous transplant), or from another party (e.g., a heterologous transplant). It should also be understood that the cellular portions of the donor material may be derived, differentiated, or otherwise isolated from primary or non-primary sources. For example, the donor material 310 may be a progenitor cell (i.e., a cell having non-proliferative or low-proliferative qualities). In another example, the donor material 310 may be a stem cell, having high proliferative and/or differentiating capacity. For instance, the donor material 310 may comprise unipotent stem cells capable of producing urothelial cells. In particular, unipotent urothelial cells may be isolated from a bladder, a ureter, a urethra, or a renal pelvis, expanded in vitro, then transferred to the receiver substrate 160.

In another example, the donor material 310 may comprise multipotent stem cells, capable of differentiating into more than one cell type. For instance, the donor material may include endoderm stem cells, or stem cells arising from an endoderm lineage. In particular, multipotent mesenchymal cells (e.g., derived from hemopoietic or adipose tissue) may be expanded and differentiated towards a urothelial fate. The resultant urothelial cells may then be transferred to the receiver substrate via the transfer beam 140. In another example, the donor material 310 may include mesoderm stem cells or stem cells arising from a mesoderm lineage. In another example, the donor material 310 may include ectoderm stem cells or stem cells arising from an ectoderm lineage. In other words, stem cells may arise from a mesodermal, endodermal, and or ectodermal origin, and may come from a common host (e.g., the host that provides intestinal tissue for cystoplasty).

In another example, the donor material 310 may comprise pluripotent stem cells capable of producing endodermic, mesodermic, or ectodermic lineages of cells. For instance, cells from the patient may be induced to become induced pluripotent stem cells (iPS). The resultant iPS cells are then expanded and differentiated into urothelial cells, which may then be transferred to the receiver substrate via the transfer beam 140.

The transfer laser 300 may be any laser known in the art used for transferring donor material 310 including but not limited to a solid-state laser, a gas laser, a dye laser, or a semiconductor laser. For example, the transfer laser 300 may be a diode pumped solid state laser. For instance, the transfer laser 300 may be a diode pumped Nd:YAG solid-state micro-laser.

The transfer beam 140 produced by the transfer laser 300 may be of any wavelength or wavelength range known in the art. For example, the transfer laser 300 may produce a transfer beam 140 in the visible spectrum (e.g., 380 to 780 nm). For instance, the transfer beam 140 may have a wavelength of approximately 532 nm. In another example, the transfer laser 300 may produce a transfer beam 140 in the near infrared spectrum (e.g., 780 to 2500 nm).

In some embodiments, the transfer beam 140 produced by the transfer laser 300 may be pulsed. The pulse rate of the transfer beam 140 may be any pulse rate or range of pulse rates known in the art. For example, the transfer laser 300 may produce a transfer beam 140 with a pulse rate ranging from 1 Hz to 10 kHz. In another example, the transfer laser 300 may produce a transfer beam 140 with a pulse rate ranging from 10 Hz to 1 kHz. For instance, the transfer laser may produce a translation beam 140 with a pulse rate of approximately 10 Hz. In another example, the transfer laser 300 may produce a translation beam 140 with a pulse rate ranging from 100 Hz to 1 kHz. For instance, the transfer laser 300 may produce a translation beam 140 with a pulse rate of approximately 1 kHz.

In embodiments, the transfer laser 300 produces a pulsed transfer beam 140 with a specific pulse length or range of pulse lengths. The pulse length of the transfer beam 140 may be any pulse rate known in the art. For example, the length of the pulse of the transfer beam 140 may range from 60 ps to 6 ns. In another example, the length of the pulse of the transfer beam 140 may range from 100 ps to 1 ns. In another example, the length of the pulse of the transfer beam 140 may be approximately 600 ps.

In embodiments, the transfer laser 300 produces a transfer beam 140 with a specific fluence or range of fluences. The fluence of the transfer beam 140 may be any range or value known in the art. For example, the fluence of the transfer beam 140 may range from 10 mJ/cm$^2$ to 10 J/cm$^2$. In another example, the fluence of the transfer beam 140 may range from 100 mJ/cm$^2$ to 1 J/cm$^2$. In another example, the fluence of the transfer beam 140 may range from 100 mJ/cm$^2$ to 500 mJ/cm$^2$. In still another example, the fluence of the transfer beam 140 may range from 300 mJ/cm$^2$ to 800 mJ/cm$^2$.

In embodiments, the transfer laser assembly 130 includes one or more optical elements configured to direct the transfer beam 140. The optical elements may be any known in the art including but not limited to mirrors, lenses, and beam-splitters. For example, the optical element may include the one or more reflecting mirrors 220. In another example, the optical element may include one or more focusing lenses 230 (e.g., an objective lens). For instance, the lens 230 may be a 75 mm achromatic lens. In another example, the optical element may be an optical attenuator 240. For example, the optical element may be a fixed attenuator plate.

In embodiments, the one or more optical elements includes an focusing lens 230. The focusing lens 230 controls the size of the ablation/removal spot upon the receiver substrate. The focusing lens 230 may be any type of lens known in the art including but not limited to an achromatic lens. For example, the focusing lens 230 may be a 150 mm achromatic lens. In another example, the focusing lens 230 may be a 75 mm achromatic lens.

In embodiments, the transfer laser assembly includes a donor substrate 320. The donor substrate 320 aids in the transfer of the donor material 310 to the receiver substrate 160. The donor substrate comprises a front surface 330. The front surface 330 faces the receiver substrate 160 and is coated with a laser absorbing layer 335 (e.g., a dynamic release layer), that absorbs laser energy. The donor substrate further includes a back surface 340 that initially receives the transfer beam 140. During LIFT, a suspension 350 containing donor material 310 is coated over the laser absorbing layer 335. When the transfer laser 300 is activated, the transfer beam 140 enters the back surface 340 of the donor substrate 320. Once the transfer beam 140 reaches the laser absorbing layer 335, localized heating at the laser absorbing layer 335 and the suspension 350 create a high-pressure vapor bubble 355 within the localized area of the suspension 350. The expansion of the vapor bubble 355 then drives the ejection of a droplet 360 of the suspension 350 towards the receiver substrate 160.

In some embodiments, the donor substrate 320 is a quartz plate. In some embodiments, the donor substrate is a fused silica plate. In some embodiments, the donor substrate is coated with a film. For example, the film may be a polymeric organosilicon compound (e.g., polydimethylsiloxane (PDMS)). In another example, the coating may be a thin gold film.

The size or range of sizes of the droplet 360 may be adjusted for the specific LIFT requirements. For example, the droplet diameter may range from 10 μm to 1 mm. In another example, the droplet diameter may range from 50 μm to 200 μm.

Figure 4:
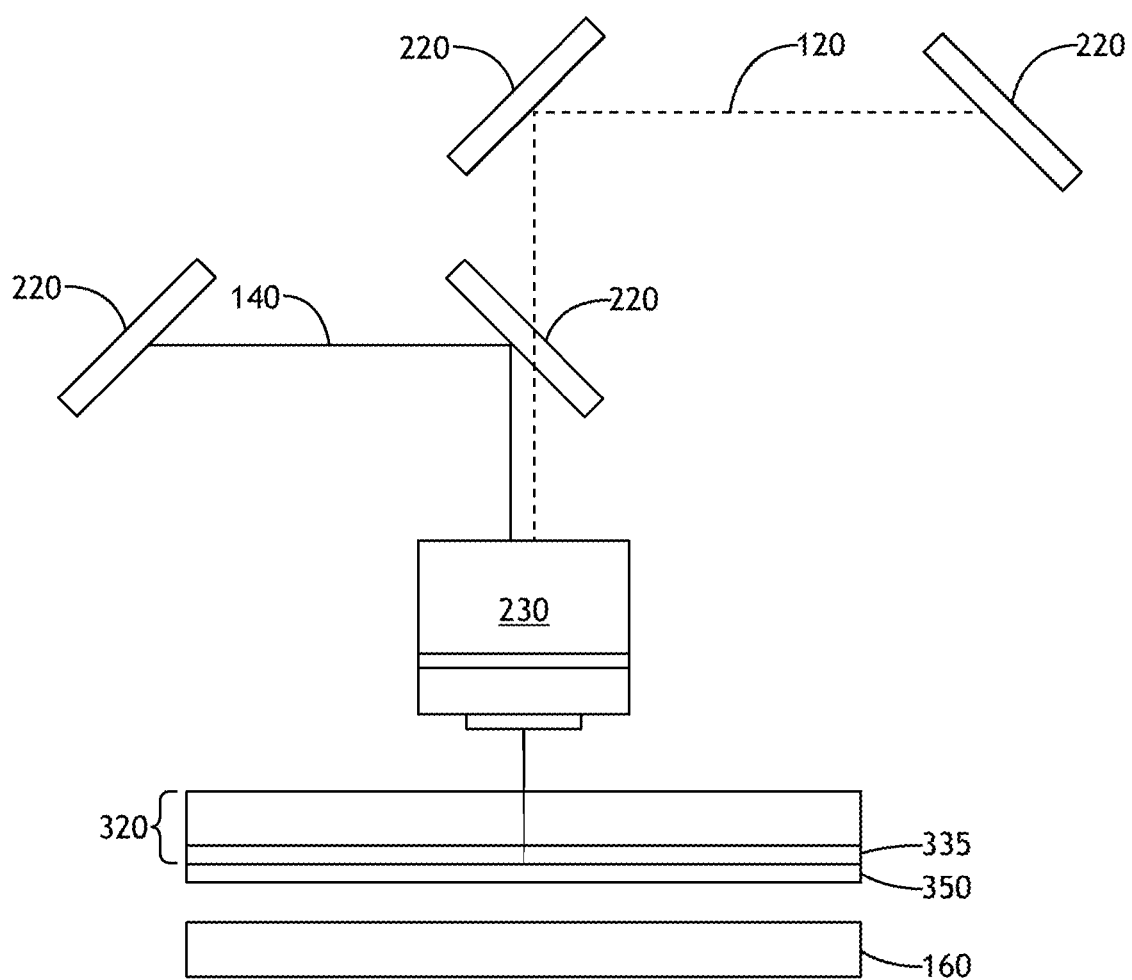
FIG. 4 illustrates a diagram of the ablation/removal laser assembly and the transfer laser assembly 130 arranged within the system, in accordance with one or more embodiments of the disclosure.

FIG. 4 illustrates a diagram of the ablation/removal laser 110 assembly and the transfer laser assembly 130 arranged within the system 100 in accordance with one or more embodiments of the disclosure. Multiple reflecting mirrors 220 direct the ablation/removal beam 120 and the transfer beam 140 to a common path 150. For example, both the ablation/removal beam 120 and the transfer beam 140 transmit through the lens 230. It should be understood that during LIFT, the transfer beam 140 is configured to focus onto the absorbing layer of the laser absorbing layer 335, and that during ablation/removal, the donor substrate 320 is typically moved out from the path of the ablation/removal beam 120, where it may focus on the receiver substrate.

Figure 5:
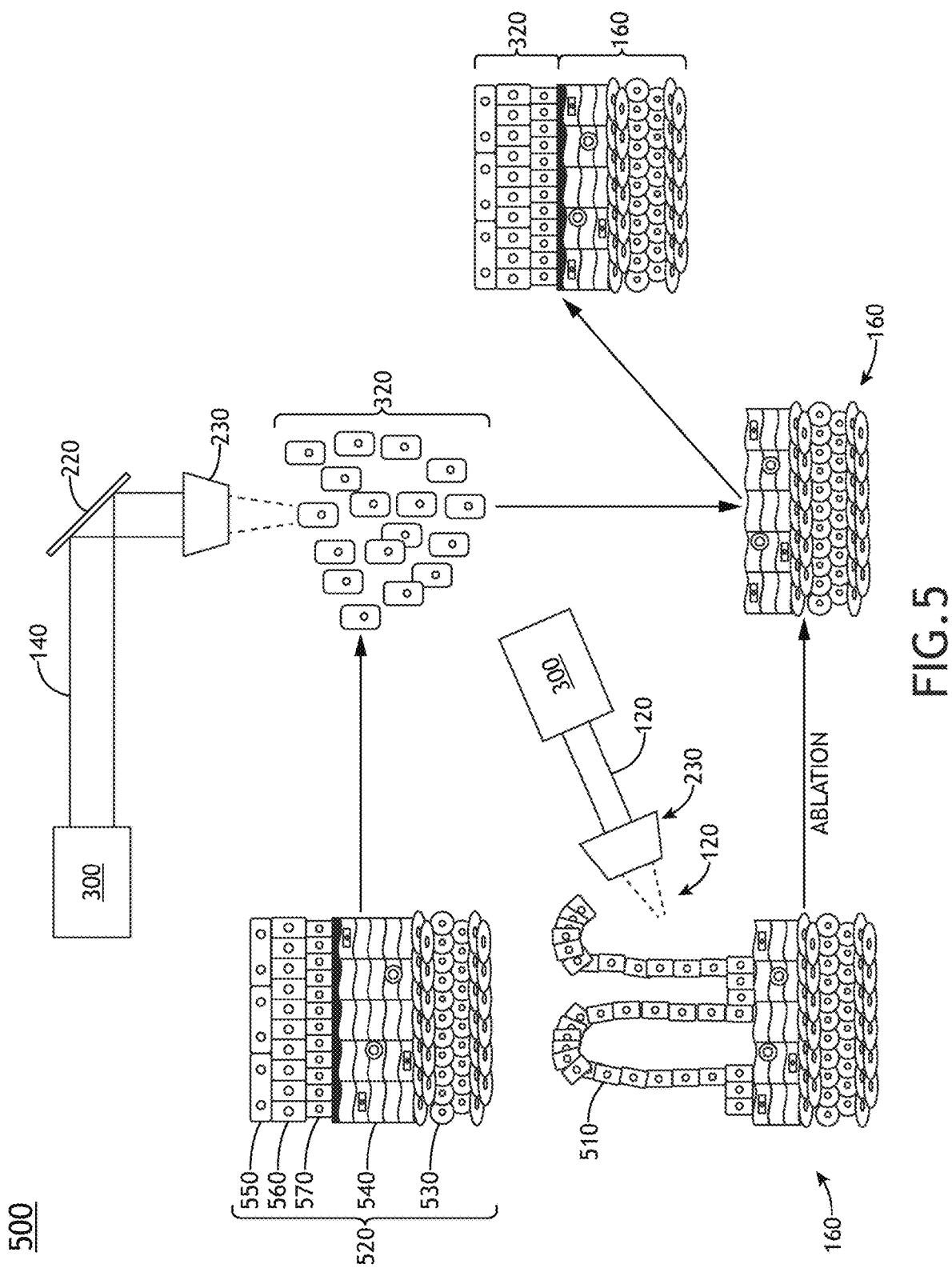
FIG. 5 illustrates a diagram of the ablation/removal and LIFT procedure using the system, in accordance with one or more embodiments of the disclosure.

FIG. 5 illustrates a diagram of the ablation/removal and LIFT procedure 500 using the system 100, in accordance with one or more embodiments of the disclosure. In some embodiments, the procedure 500 includes the preparation of the receiver substrate 160. For example, the receiver substrate 160 may be intestinal tissue surgically removed from the patient, as shown in FIG. 5. The internal layer of intestinal tissue contains an epithelial layer 510 of epithelial cells arranged in thread-like projection (i.e., villi). The epithelial cells absorb nutrients and secrete mucus, making the cells incompatible for augmentation cystoplasty. The intestinal epithelial cells are then removed from the intestinal tissue via the ablation/removal beam 120 produced by the ablation/removal laser 200. The ablation/removal removes the epithelial cells (e.g., denudes the epithelial cells), but does not remove the smooth muscle layer or other connective tissues that give structure to the intestinal tissue. In this manner, the ablation/removal of epithelial cells exposes a target layer for the placement of donor material.

In some embodiments, the preparation of the receiver substrate 160 may further include enzymatic treatment. Any enzyme used in preparation or the receiver substrate 160 may be any enzyme known. For example, the receiver substrate 160 may be treated with a cell dissolution enzyme (e.g., trypsin). For instance, the receiver substrate may be treated with the commercial trypsin product TrypLE (Gibco).

In some embodiments, the preparation of the receiver substrate 160 may further include mechanical treatment. For example, receiver substrate 160 may be scraped with an instrument (e.g., a scalpel), partially and/or entirely removing cells or debris from the receiver substrate. In some embodiments, the preparation of the receiver substrate 160 may include both enzymatic treatment and mechanical treatment. For example, the receiver substrate 160 may first be treated with cell dissolution enzyme, then scrapped with an instrument.

In some embodiments, the procedure includes the preparation of the donor substrate 320. For example, the donor substrate 320 may include urothelial cells (e.g., donor material) isolated from a urothelium 520 of the patient. Urothelial cells may also be isolated from other tissues or differentiation processes as described above. The urothelium 520 includes several tissue layers, including a muscle layer 530 and stromal layer 540 that give structure and rigidity to the bladder. Urothelial cells proliferate between the stromal layer and the interior surface of the bladder. The urothelial cells are themselves stratified into layers. Fully differentiated urothelial cells 550 (e.g., umbrella cells) are disposed as the surface layer of epithelial-like cells on the interior wall of the bladder. Underneath the umbrella cells are intermediate cells 560 that will eventually mature to become umbrella cells. At the base of the urothelial layer are basal urothelial cells 570. A portion of the basal urothelial cells 570 have stem cell-like qualities and are capable of self-renewal and/or proliferation, making these cells particularly valuable for transplantation. Once attached to an exposed area of a receiving substrate, the basal urothelial cells 570 proliferate, eventually creating a multilayered stratum of urothelial cells similar to the urothelium 520.

The urothelial cells may be isolated from the urothelium 520 by any means known in the art including scraping, enzymatic dissociation, or a combination of scraping and enzymatic dissolution. For example, a portion of the urothelium 520 may be treated with a dissolution enzyme (e.g., dispase II), then gently scraped with a scalpel to remove the dissociated cells. The dissociated cells may then be washed and used directly for the LIFT procedure, or may be cultured in vitro to expand the number of cells for transplantation.

In embodiments, the procedure includes the transfer of the donor material 310 (e.g., the isolated urothelial cells) onto the receiver substrate 160 via LIFT. The urothelial cells are placed within the path a transfer beam 140 produced by the transfer laser 300, ejecting the cells onto the exposed target layer of the receiver substrate 160 produced by the ablation/removal laser. After transplantation by LIFT, the urothelial cells proliferate, eventually creating a mature striated layering of urothelial cells.

Figure 6:
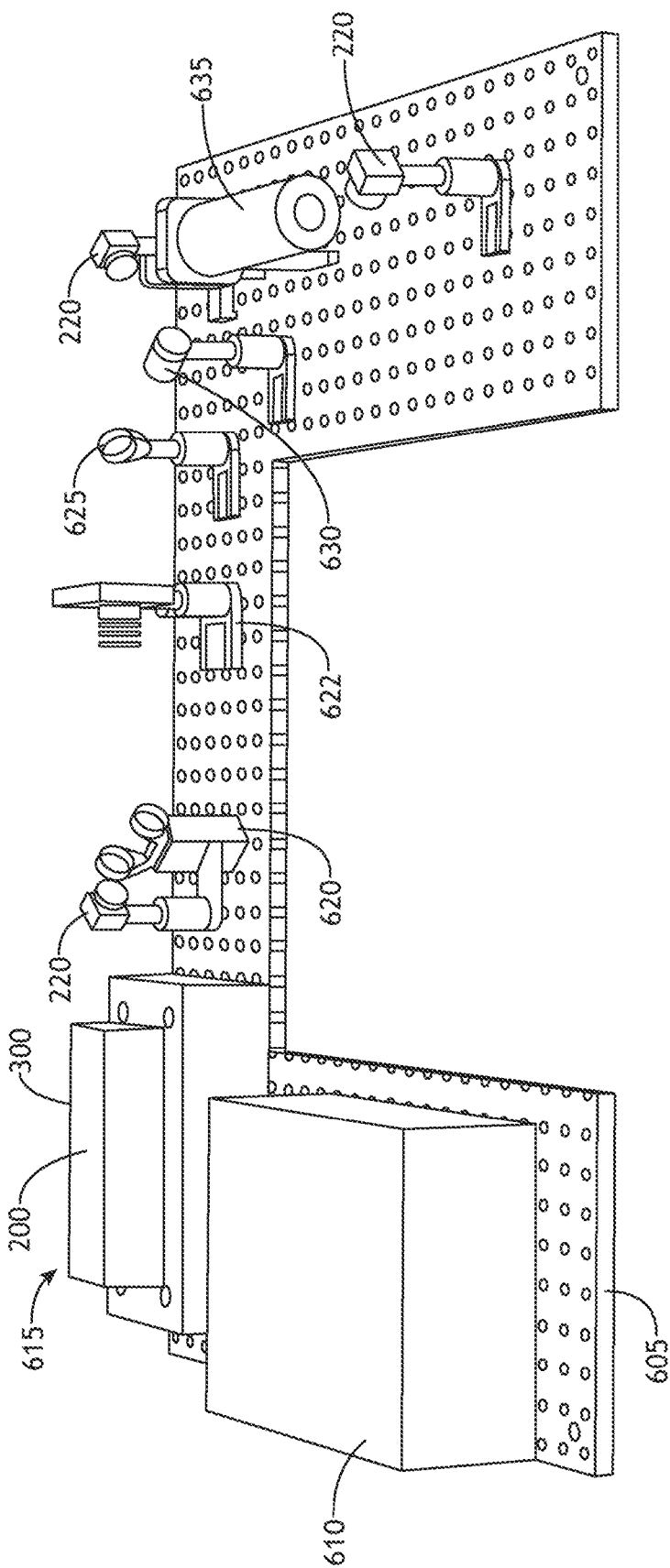
FIG. 6 illustrates a diagram of support and componentry for the system, in accordance with one or more embodiments of the disclosure.

FIG. 6 illustrates a diagram of support and componentry for the system 100 in accordance with one or more embodiments of the disclosure. In embodiments, the system includes a top breadboard 605. The top breadboard may be aluminum and further include holes (e.g., M6 threads) to support system componentry. The system may include a laser controller 610 positioned near the ablation/removal laser 200 and the transfer laser 300 (e.g., the ablation/removal laser 200 and the transfer laser 300 may be disposed within a single housing 615. The laser controller 610 controls one or more parameters of the laser (e.g., power and/or pulse rate).

In embodiments, the system 100 further contains a flip mount 620 disposed adjacent to the ablation/removal laser 200 and the transfer laser 300. The flip mount 620 includes two flip-mount mirrors, each one reflecting one wavelength and absorbing the other, and vice versa. In this manner, the system 100 may switch from ablation/removal activity to LIFT activity. In embodiments, the flip mount 620 is motorized.

In embodiments, the system further includes a rotator 622, a polarizer 625 and a beam dump 630. The polarizer is configured to be set at a Brewster's angle. The beam dump 630 is configured to effectively trap the portion of the beam that is reflected from the polarizer 625. In embodiments, the system 100 further includes a beam expander 635 to magnify the beam. Multiple reflecting mirrors 220 are used to direct the ablation/removal beam 120 and the transfer beam 140.

Figure 7:
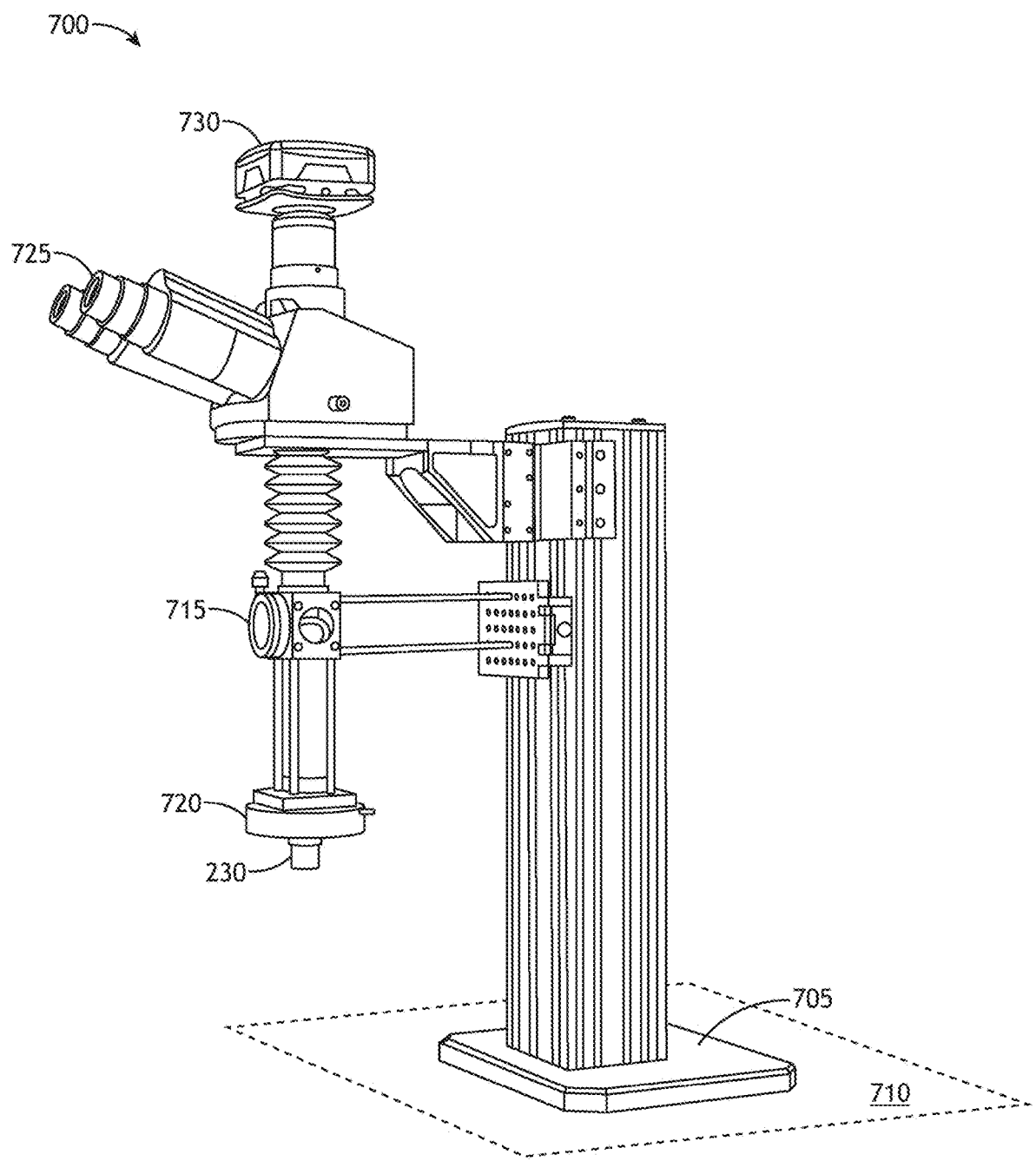
FIG. 7 illustrates a diagram of an optical tower of the system, in accordance with one or more embodiments of the disclosure.

FIG. 7 illustrates a diagram of an optical tower 700 for the system 100 in accordance with one or more embodiments of the disclosure. The optical tower 700 is utilized for both the LIFT procedure and imagery purposes. In embodiments, the system optical tower 700 includes an optic rail 705 mounted to a base breadboard 710 that supports the elements of the optical tower 700. The optical tower 700 further includes a beam splitter 715 that directs the ablation/removal beam 120 and/or the transfer beam 140 to the focusing lens 230.

The optical tower further includes a light source 720 mounted coaxially with the microscope objective or a focusing lens. The light source 720 is configured to illuminate the receiver substrate 160 and/or the donor substrate 320, allowing observance by the eyepiece 725 (e.g., trinoculars) and/or a camera 730 (e.g., a CCD camera). The light source 720 may include any type of light source known in the art including but not limited to a light emitting diode.

Figure 8:
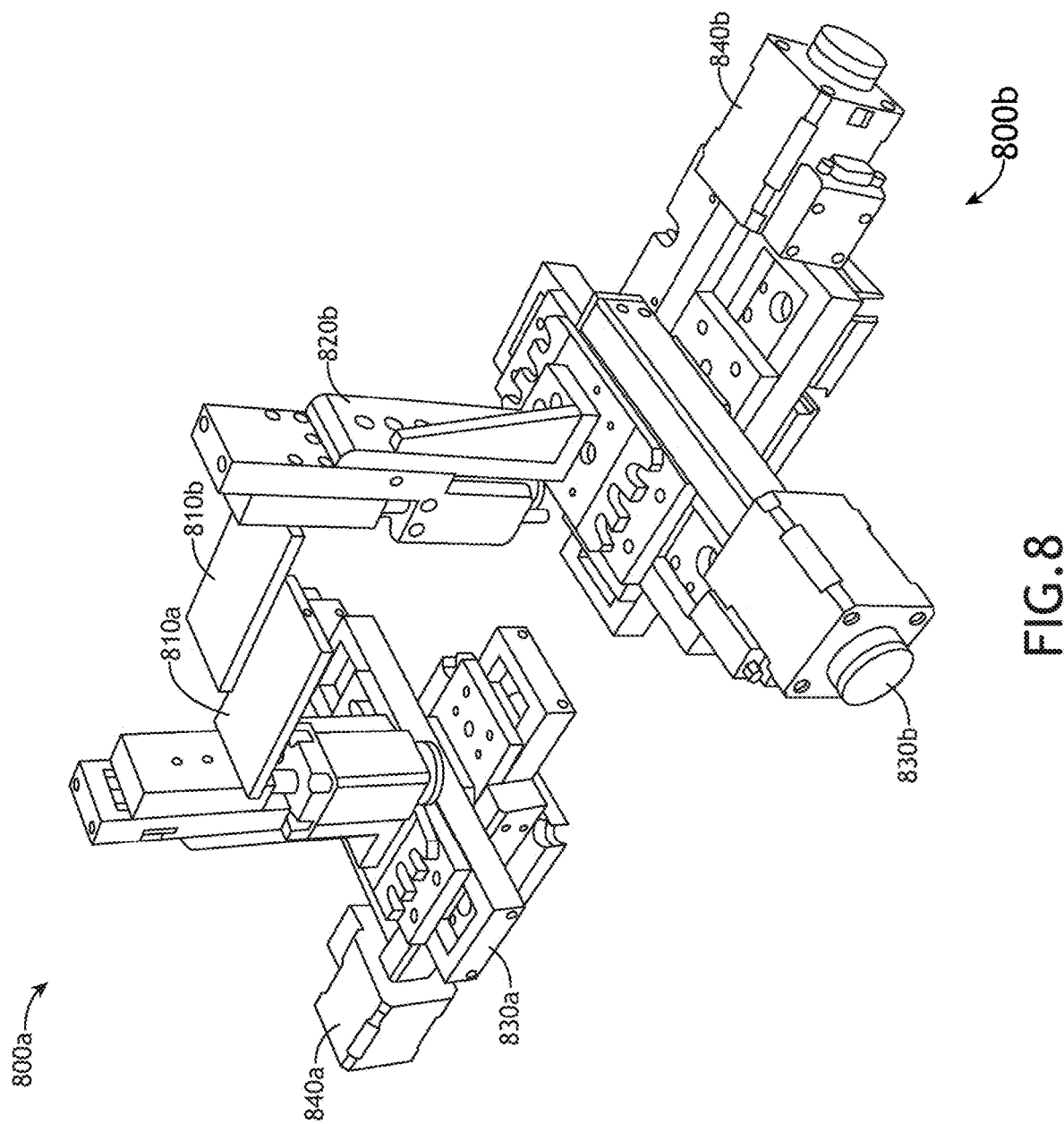
FIG. 8 illustrates a diagram of two translation stage assemblies for the system, in accordance with one or more embodiments of the disclosure.

FIG. 8 illustrates a diagram of two translation stage assemblies 800a, 800b for the system 100 in accordance with one or more embodiments of the disclosure. The two translation stage assemblies 800a, 800b are arranged so that the receiver substrate 160 is mounted to one of the translation stage assemblies 800a, while the donor substrate 320 is mounted to the other translation stage assembly 800b (e.g., one of the translation stage assemblies 800a, 800b is adapted to support the donor substrate 320, while the other of the translation stage assemblies 800a, 800b is adapted to support the receiver substrate 160). In embodiments, each translation stage assembly 800a, 800b includes a mounting surface 810a, 810b that are coupled to a first translatable stage 820a, 820b translatable on a z-axis. The first translatable stage 820a, 820b is coupled to a second translatable stage 830a, 830b and a third translatable stage 840a, 840b configured for X-axis and Y-axis translation. It should be understood that the first translatable stage 820a, 820b, second translatable stage 830*a*, 830*b*, and/or third translatable stage 840*a*, 840*b* may be motorized. It should also be understood that any configuration of translation stages may be used to for X-axis, Y-axis, and Z-axis movement of the donor substrate 320 or the receiver substrate 160. Therefore, the above description is not intended to be a limitation of the present disclosure, but merely an illustration.

Figure 9A:
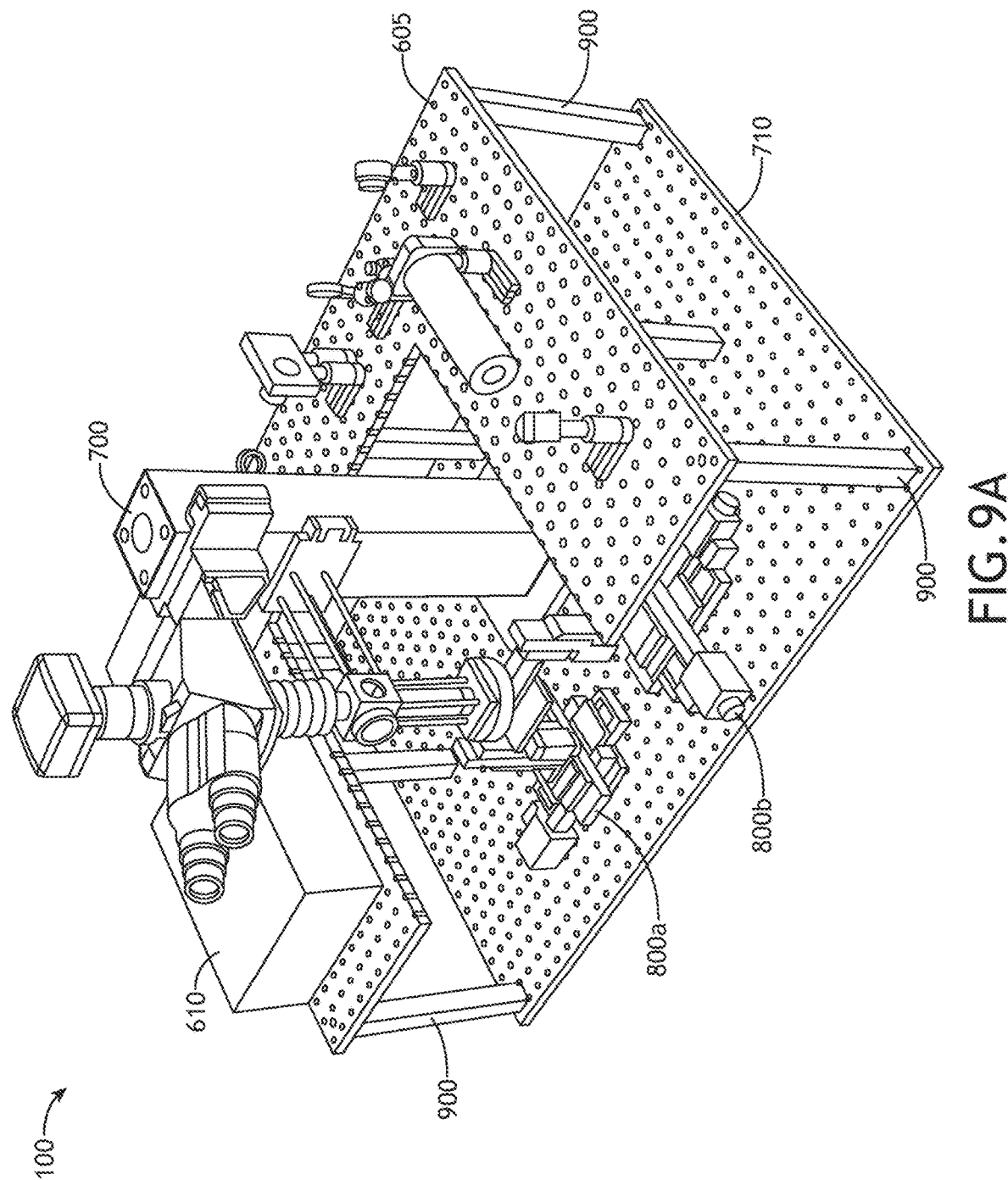
FIG. 9A illustrates a diagram of a system for ablation/removal and transfer of material, in accordance with one or more embodiments of the present disclosure.

FIG. 9A illustrates a diagram of the system 100, in accordance with one or more embodiments of the disclosure. The top breadboard 605 is mounted onto the base breadboard via one or more columns 900. The optical tower 700 and the translation stage assemblies 800*a*, 800*b* are mounted to the base breadboard 710.

Figure 9B:
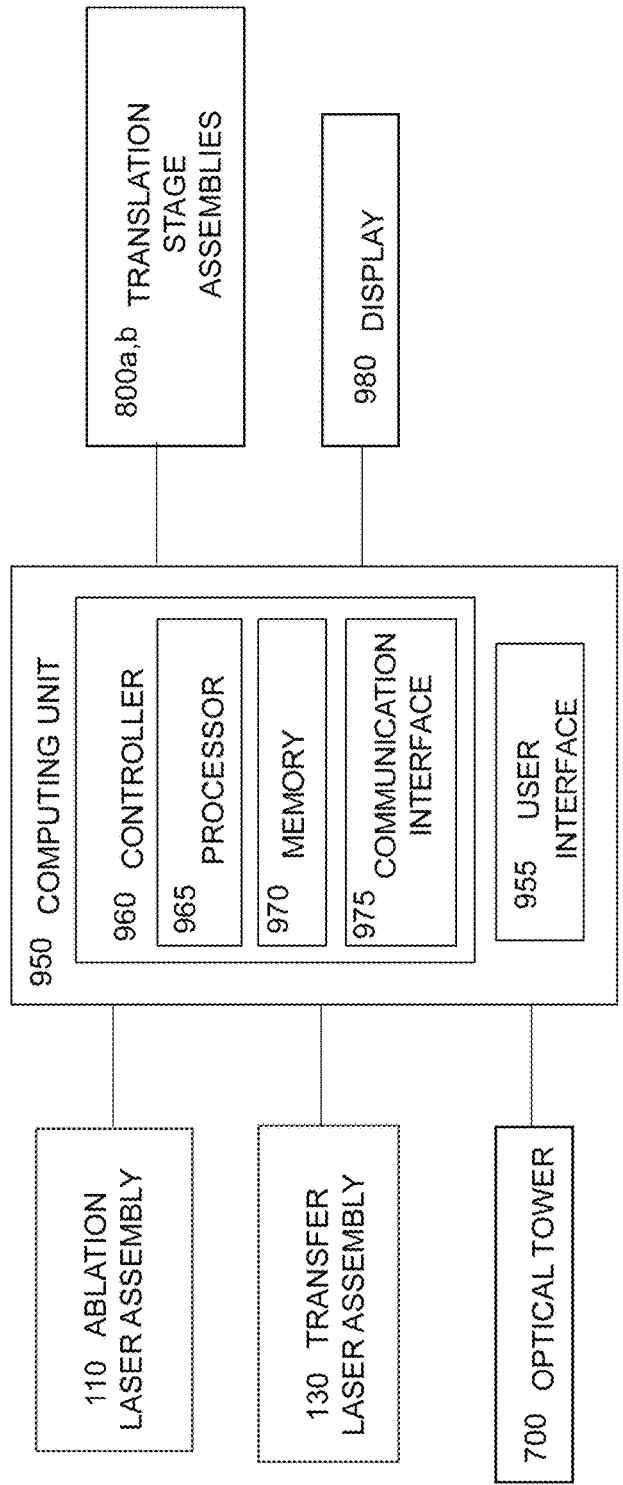
FIG. 9B illustrates a block diagram of the system, in accordance with one or more embodiments of the disclosure.

FIG. 9B illustrates a block diagram of the system 100, in accordance with one or more embodiments of the disclosure. In some embodiments, the system 100 includes a computing unit 950. The computing unit 950 automates and/or controls one or more functions of the system 100. For example, the computing unit 950 may be configured to automate the movement of the translational stage assemblies 800*a*, 800*b*. In another example, the computing unit 950 may be configured to control the switching on and off of the ablation/removal laser 200 and/or the transfer laser 300. The computing unit 950 may be configured as any device capable of automating and/or controlling componentry of the system. For example, the computing unit 950 may be a desktop computer. In another example, the computing unit 950 may be a laptop computer.

In embodiments, the computing unit 950 further includes one or more user interfaces 955. The user interface 955 is configured to receive input from a user. The one or more user interfaces 955 may include one or more input devices that may include any user input device known in the art. For example, the one or more input devices may include, but are not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device, or the like.

In embodiments, the computing unit 950 includes a controller 960, being in communication of with the computing unit 950 and other components of the system 100. The controller 960 is configured to receive, process and transmit data within the system 100. The controller 960 includes one or more processors 965 configured to perform functions or steps according to program instructions stored in a memory 970. memory 970. The controller is further configured to include a communication interface 975. The communication interface 975 is configured to facilitate data transfer between components of the system computing unit 950 and/or the system 100.

The one or more processors 965 may include any type of processing elements, including but not limited to integrated circuits (e.g., application specific integrated circuits (ASIC) and field programmable gate arrays (FPGA). The memory 970 may also include resident or external memory for storing data, executional code, and other resident or external memory generated by the system 100. The controller 960 can execute one or more software programs embodies in a non-transitory computer readable medium (e.g., memory 970) that implement techniques described herein. In some embodiments, the controller 960 is not limited by the materials from which it is formed or the processing mechanisms employed therein and, as such, can be implemented via semiconductor(s) and/or transistors (e.g., using electronic integrated circuit (IC) components), and so forth.

The memory 970 can be an example of tangible, computer-readable storage medium that provides storage functionality to store various data and/or program code associated with operation of the system 100 and/or controller 960, such as software programs and/or code segments, or other data to instruct the controller 960, and possibly other components of system 100, to perform the functionality described herein. Thus, the memory 970 can store data, such as a program of instructions for operating the main controller 960 and other components of the system 100. It should be noted that while a single memory 970 is described, a wide variety of types of combinations of memory 970 (e.g., tangible, non-transitory memory) may be employed. The 970 can be integral with the controller 960, can comprise stand-alone memory, or can be a combination of both. Some examples of the memory 970 can include removable and non-removable memory components, such as random-access memory (RAM), read-only memory (ROM), flash memory (e.g., a secure digital (SD) memory card, a mini-SD memory card, and/or a micro-SD memory card), solid-state drive (SSD) memory, magnetic memory, optical memory, universal serial bus (USB) memory devices, hard disk memory, external memory, and so forth.

The communication interface 975 can be operatively configured to communicate with componentry within the system 100. For example, the communication interface 975 may be configured to retrieve data from the controller 960, transmit data for storage in the memory 970, retrieve data from storage in the memory 970, and so forth. The communication interface 975 can also be communicatively coupled with the controller 960 to facilitate data transfer between components of the system 100 and the controller 960. For example, the communication interface 975 may be communicatively coupled with the translation stage assemblies 800*a*, 800*b*. For instance, the controller 960, via the communication interface 975, may be configured to direct one of the translation stage assembly 800, 800*b* to align the receiver substrate 160 to a focal place of the focusing lens 230 (e.g., the objective lens).

In another instance, the controller 960, via the communication interface 975, may be configured to direct at least one of the translation stage assemblies 800*a*, 800*b* or the one or more beam control elements to ablate/remove a portion of the receiver substrate 160 to expose a target layer of the receiver substrate 160. In another instance, the controller 960, via the communication interface 975, may be configured to direct at least one of translation stage assemblies 800*a*, 800*b* to align the front surface of the donor substrate 320 to be parallel to and facing the receiver substrate 160, with the coating on the donor substrate 320 located at the focal plane of the focusing lens 230. In still another instance, the controller 960, via the communication interface 975, may be configured to direct at least one of translation stage assemblies 800*a*, 800*b* or the one or more beam control elements to irradiate the coating through the back surface 340 of the donor substrate 320 to transfer a portion of the donor material to the target layer of the receiver substrate 160.

The communication interface 975 can also be communicatively coupled with the controller 960 to facilitate data transfer between other components of the system 100 and the controller 960. For example, the communication interface 975 may be communicatively coupled with the ablation/removal laser assembly 110, the transfer laser assembly 130, and the optical tower 700. For instance, the controller 960, via the communication interface 975 may be configured to facilitate instructions from the controller 960 to autofocusing componentry within the optical tower 700. In another instance, the controller 960, via the communication interface 975 may be configured to transfer data to a display 980.

Figure 10A:
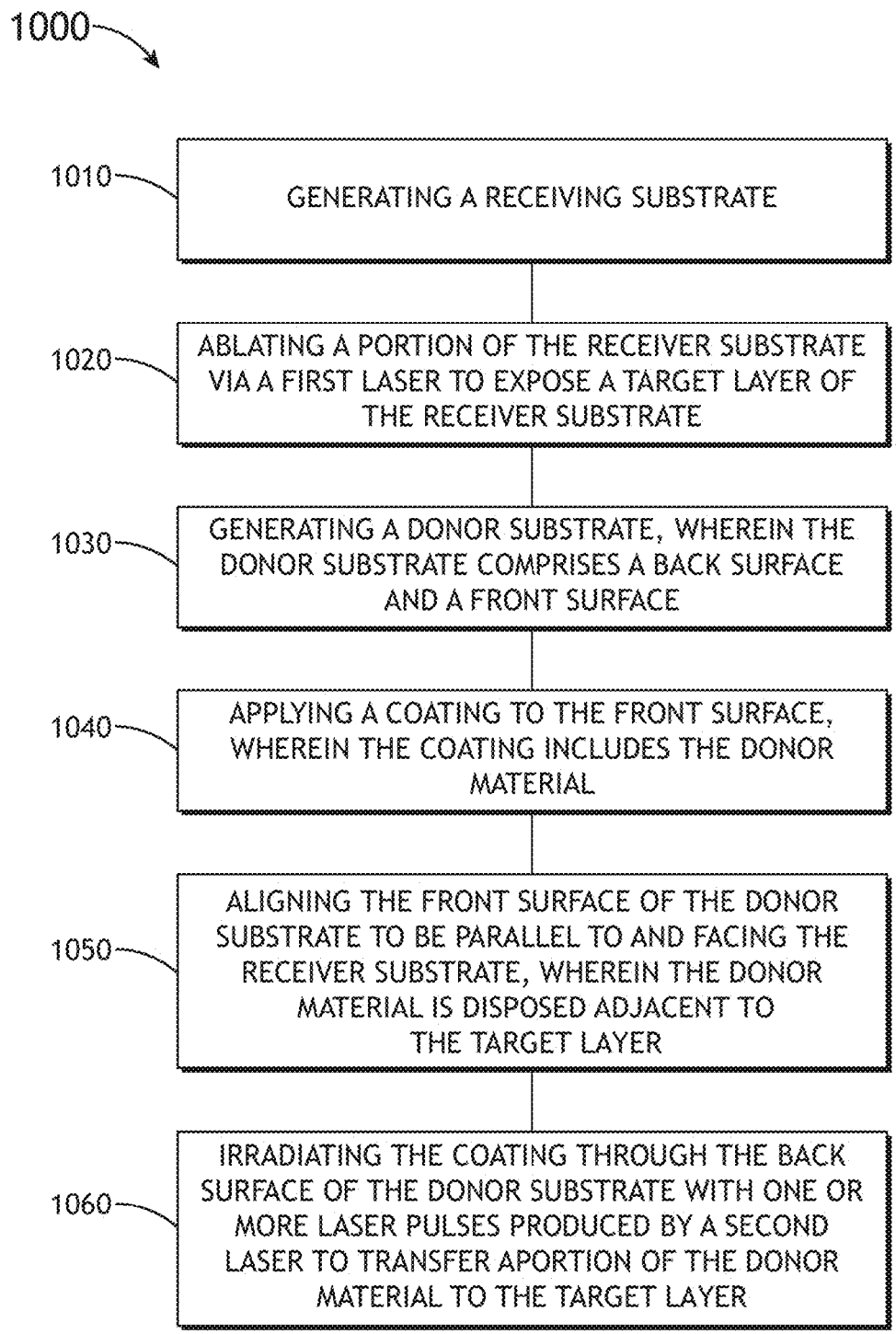
FIGS. 10A and 10B. Illustrate a flow diagram of a method for ablating and transferring material, in accordance with one or more embodiments of the present disclosure.
Figure 10B:
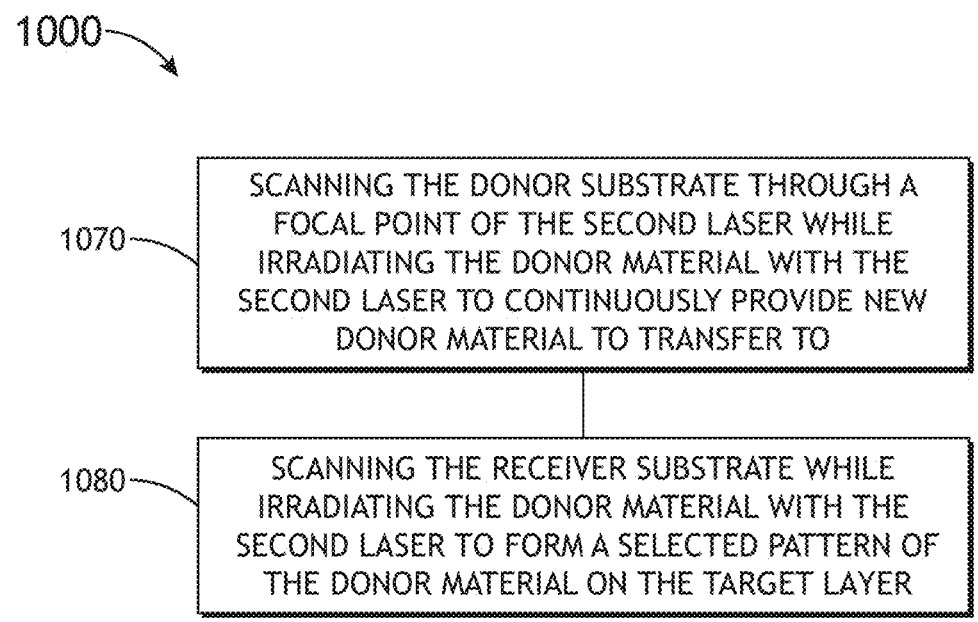

FIGS. 10A and 10B illustrate a method 1000 for ablating a receiver substrate and transferring donor material, in accordance with one or more embodiments of the disclosure. Accordingly, method 1000 may include any step expressed or implied by the foregoing embodiments of the system 100. Further, it is contemplated that one or more steps of method 1000 may be executed by a system or device known to the art beyond those described above. As such, method 1000 should be understood to encompass any configuration for carrying out the following steps.

In embodiments, the method comprises a step 1010 of generating the receiver substrate 160. The receiver substrate 160 may be produced by any methods and materials as described herein. The method 1000 further includes a step 1020 of ablating a portion of the receiver substrate via a first laser to expose a target layer of the receiver substrate. The first laser is configured as the ablation/removal laser 200 that produces the ablation/removal beam 120.

The method 1000 further includes a step 1030 of generating the donor substrate 320, wherein the donor substrate 320 comprises a back surface 340 and the front surface 330. The method 1000 further includes a step 1040 of applying a coating to the front surface 330, wherein the coating includes donor material 310. For example, the donor material 310 may include urothelial cells from the urothelium 520.

The method 1000 further includes a step 1050 of aligning the front surface 330 of the donor substrate 320 to be parallel to and facing the receiver substrate 160, wherein the donor material 310 is disposed adjacent to the target layer. The alignment may be performed by the translation stage assemblies 800a, 800b.

The method 1000 further includes a step 1060 of irradiating the coating through the back surface 340 of the donor substrate 320 with one or more laser pulses produced by a second laser to transfer a portion of the donor material to the target layer. In embodiments, the second laser is the transfer laser 300 that produces a transfer beam 140.

In embodiments, the method 1000 further includes a step 1070 (e.g., continuing from FIG. 10A to FIG. 10B) of scanning the donor substrate 320 through a focal point of the second laser while irradiating the donor material 310 with the second laser to continuously provide new donor material to transfer to the receiver substrate 160. By moving/translating the donor substrate 320 along the same plane as the receiver substrate 160, the donor substrate 320 can keep supplying donor material 310 from the coating until the donor material from the coating is depleted.

The method 1000 further includes a step 1080 of scanning the receiver substrate 160 while irradiating the donor material 310 with the second laser to form a selected pattern of the donor material 310 on the target layer. The selected pattern may include one, or more than one, layers of donor material 310 that has been deposited on the target layer.

The following examples are intended only to further illustrate the invention and are not intended to limit the scope of the subject matter which is defined by the claims.

EXAMPLE 1

Isolation of Murine Urothelial Cells

In a first instance of urothelial cell isolation, Krt5CreERT2-R26td-Tomato mice were initially injected with 3 mg Tamoxifen daily for 5 consecutive days. In this genetic model, upon tamoxifen injection, the majority of KRT5-positive cells express the Tomato fluorescence protein (i.e., KRT5 is a marker for stratified epithelium/urothelium). Primary urothelial cells were isolated from surgically removed bladder specimens as follows: bladders were dissected after the cutting off the ureters and the urethra. Bladders were subsequently turned inside-out to expose the urothelium 520. Following rinsing with PBS, bladders were submerged in growth media supplemented with in 5 mg/ml dispase II and incubated at 37° C. for 1 hour. Following dispase dissociation, the urothelial layers were gently scraped off with the use of scalpels. Single cell suspensions were generated by pipetting up and down for at least 5 minutes. Cells were counted and processed for direct printing or in vitro expansion. The medium that was used is 1:1 mixture of MDCB153/advanced Dulbecco's modified essential medium (supplemented with 0.1 mM ethanolamine (Sigma), 0.1 mM phosphoethanolamine (Sigma), 0.5 µg/ml-1 hydrocortisone (Sigma), 5 µg/ml-1 insulin (Sigma), 15 µg/ml-1 adenine (Sigma), 100 U/ml-1 penicillin and 100 µg/ml-1 streptomycin) and V79 lung fibroblast conditioned medium.

In a second instance of urothelial cell isolation, Krt5CreERT2-R26td-Tomato mice were injected intraperitoneally with 3 mg tamoxifen (Sigma) daily, for 5 consecutive days. Labeling efficiency of KRT5 positive cells (red fluorescence) was 63.5% of the total basal urothelial cell population. The Tamoxifen-injected mice (at least 72 hours after last tamoxifen injection) were sacrificed by cervical dislocation and placed on clean and sterile workstation inside a hood with light and ventilation turned don. The murine abdominal skin was then sterilized with 70% Ethanol (EtOH) solution in double distilled water. The lower abdominal skin was uplifted with clean (sterile) forceps and cut open with scissors, just above genitals, to expose the bladder. With new sterile forceps, the bladder was uplifted vertically by its dome. Using new sterile scissors, the bladder was excised by cutting off the ureters and the urethra just below the bladder neck. The bladder was then transferred to sterile paper to drain urine. Immediately afterward, the bladder was washed in sterile phosphate buffer solution (PBS) in a sterile culture dish for several seconds, then soaked into new sterile culture dish with PBS at room temperature (RT). The process was repeated for up to 10 bladders, with approximately 10 minutes transpiring between first and last bladder isolation.

The culture dish with isolated bladders was transferred under a stereoscope. Using sterile forceps, each bladder was everted through the neck of the bladder. The everted bladders were placed in sterile 15 ml tubes with sterile 5 mg/ml dispase II (Sigma) in Advance DMEM (Sigma) medium (two bladders per ml) and incubated at 37° C. for one hour. Next, the bladders were washed from dispase II by submerging them for few seconds consecutively in three culture dishes containing PBS supplemented with 5% FBS (PBS-FBS) and collected in a final culture dish with 10 ml of PBS-FBS.

Primary urothelial cells were collected by gently scraping with a scalpel blade under stereoscope, leaving the muscle and lamina propria layers intact. The remaining bladder tissues were discarded. The scraped urothelial cell sheets were further dissociated mechanically to single cells by intense pipetting up and down for 5 min using 10 ml sterile pipette within a cell culture hood. The cells were then transferred through a 70 µm cell strainer into 50 ml sterile conical tubes and filled up completely with additional PBS-FBS. The cells were then centrifuged (e.g., 1500 rpm for 5 min) and the supernatant was carefully discarded. The cells were re-suspended and centrifuged twice in 50 ml PBS-FBS under the same conditions. The washed urothelial cells were then resuspended in 1 ml growth medium (1:1 mixture of MDCB153/advanced Dulbecco's modified essential medium (1:1 mixture of MDCB153 and advanced Dulbecco's modified essential medium (Sigma), supplemented with 0.1 mM ethanolamine (Sigma), 0.1 mM phosphoethanolamine (Sigma), 0.5 mg/ml hydrocortisone (Sigma), 5 mg/ml insulin (Sigma), 15 mg/ml adenine (Sigma), 100 U/ml penicillin and 100 mg/ml streptomycin) and V79 lung fibroblast conditioned medium) and the viable cells were counted with a haemocytometer (Trypan blue exclusion). A successful implementation yielded ~2×10$^6$ cells (out of 10 bladders) and a reddish cell pellet (due to Tomato positive cells). The cell pellet would be atypically white if the protocol is implemented for non-labeled cells (wild-type or any other unlabeled mouse strain).

EXAMPLE 2

Expansion, Freezing, and Thawing of Urothelial Cells

To expand primary urothelial cells in typical 2-D cultures, 1×10$^5$ or 8×10$^5$ isolated primary urothelial cells were placed into 12-well plates or 60 mm dishes, respectively, containing growth medium and incubation at 37° C. and 5% $CO_2$ atmosphere. The dishes were labeled as passage zero (P0). The next day, most cells were attached to the cell culture dish and confer an epithelial morphology. Some debris and floating-dead-cells were also evident. Small cell clusters (colonies) were visible throughout the dish one day later. The medium was replaced the first morning after seeding and every two days onwards. The cells were passaged when reaching ~90% confluence utilizing trypsin (e.g., TrypLE (ThermoFisher Scientific)) as follows: the medium of a confluent dish was aspirated and the cells were washed once with sterile PBS. Then, appropriate volume of trypsin was added. The dishes were incubated at room temperature inside the hood and investigated under optical microscope every few minutes. At ~3 min most of the cells become fully rounded but still attached on the culture dish. 5-10 minutes later, with the aid of tapping, >80% of the cells were fully detached. Next, medium was added (900 µl/12-well plate or 1750 µl/6-well plate) and the remaining attached cells were detached with a cell scraper. The cells were then transferred into sterile and labeled 15 ml tubes and supplemented with growth medium up to 5 ml total volume. The cells were then centrifuged at 1000 rpm for 5 min at RT.

After centrifugation the supernatant was carefully discarded. Cell pellets were resuspended at appropriate volume of growth medium and passaged into new sterile and labeled dishes at 1:4 ratio. The cells grow indistinctly for the first 3 passages (3-5 days to reach confluency). Then they start to grow with slower growth rate (1-2 days more for confluency) for the next 1-2 passages and after 5th passage they grow at distinct colonies but not throughout the culture area and become exhausted before reaching confluence.

Of note, several other passaging enzymes were investigated but with less effective outcome. In more detail, 5-10 min 0.5% v/v dispase II treatment before cell scrapping yielded~half of the abovementioned viable and attached cells the next day. Use of trypsin/EDTA solution of various concentrations (0.005-0.05%) and various durations (3-15 min) yielded 10-20% of the abovementioned viable and attached cells the next day. Collagenase type IV for 10 min followed by scraping was also poorly effective (>10% of TrypLE effect) for passaging the cells. Similarly ineffective was the use of ReLeSR™. The commercially available KGM Gold medium was also tested for culturing primary urothelial cells but its use was finally aborted. Although it was quite similar to the abovementioned one during the expansion of P0 cells, showing a small delay (~24 h) in reaching confluency, after the first passage the number of attached cells and their growth kinetics were severely shorter.

Primary urothelial cells can be frozen (e.g., cryopreserved) in liquid N2. During cell passage, ¼ of the cells from a confluent dish in 500 µl of growth medium can be transferred into a cryovial and mixed with 2× cryopreservation medium (80% FBS and 20% DMSO). The cryopreserved cells were labeled and considered after thawing to be one passage older when confluency was reached (i.e., P0 cryopreserved cells were labeled as P1 cells). Then the cryovial should be transferred into a freezing container (NALGENE) and placed at −80° C. for 24 h before moving to liquid N2.

Cryopreserved primary urothelial cells can be thawed in water bath at 37° C. and immediately transferred into 15 ml tube containing 5 ml of growth medium. After centrifugation at 1000 rpm for 5 min at room temperature, the supernatant was removed and the cell pellet was resuspended in appropriate volume of growth medium. Then the cells were seeded into culture dish of the same size as the one they were detached prior cryopreservation. Cryopreserved cells of P0 and P1 passages were successfully thawed and grown indistinguishably to the freshly isolated and continuously cultured ones up to P4. They also retain the capacity to form spheres in Matrigel (Corning Life Sciences).

EXAMPLE 3

Growth of Primary Urothelial Spheres in Matrigel

Freshly isolated primary urothelial cells as well as cultured ones up to P4 or thawed primary cells at P0 or P1 at a density of 1×10$^4$ cells per µl of growth medium were mixed with 39-µl ice-cold Matrigel and plated onto clean sterile glass coverslips in 24-well plate as a single drop without bubbles. The 24-well plate was covered and incubated at 37° C. and 5% CO2 atmosphere for 20 min to allow Matrigel to solidify. 500 µl of growth medium then was added slowly to each well without disturbing the Matrigel. Medium was carefully changed every two days and the formation and growth of spheres was monitored through an optical microscope. Typically, small sphere formation (sum of few cells) was evident by day two or three.

EXAMPLE 4

Preparation of Intestinal Tissue

For isolation of intestinal tissue (e.g., containing smooth muscle tissue), eight-week-old donor mice were scarified by cervical dislocation and placed on a clean and sterile workstation inside a ventilation hood with light and ventilation turned on. After stabilizing the body with tape on its four legs and tail, the abdominal skin was sterilized with 70% (EtOH) solution. With a clean and/or sterile forceps, the lower abdomen skin was uplifted and scissors were used to cut the skin open in order to expose the internal organs. With sterile forceps, the intestine was progressively uplifted while with another sterile pair of scissors simultaneous mesenteric excision was performed. During the process, special caution was undertaken in order to avoid any contact of the intestinal tissue with the scissors and forceps. If the intestinal tissue was contacted with other non-sterile material or external mouse body parts (e.g., skin) the process was canceled and reinitiated with another donor mouse after complete sterilization of the workstation.

After mesenteric excision, intestine was completely excised with two cross sections approximately five to seven cm away from the forceps on either side, releasing an intestinal tissue fragment of at least 10 cm long, which was placed on a clean and/or sterile culture dish. Then, a catheter was inserted in one end of the intestinal fragment with caution not to damage the tissue with the aid of the forceps, which was also used to maintain the catheter in position. 200-250 ml of saline or PBS was allowed to flow through the intestinal fragment while keeping the intestinal fragment vertical in the air above a dean sterile bucket where the drained material was collected and discarded. The clean tissue was then submerged in a culture dish (100 mm diameter) containing 15 ml sterile PBS supplemented with gentamycin and amphotericin B (PBS+GA, 50 μg/ml and 2.5 μg/ml final concentrations, respectively). There, the intestinal fragment was cut into small tubular pieces approximately one cm long. Each small tubular piece was then transferred into a new sterile 60 mm culture containing PBS+GA. Then, under a stereoscope the each of the small tubular pieces were cut across with sterile scissors to lose their tubular shape. Removal of the epithelial layer from these intestinal tissues may be performed using laser ablation/removal, enzymatic/chemical dissociation, or mechanical scraping. For mechanical scraping, curved-end sterile forceps were used to stabilize flattened tissue on one of its four corners with the intestinal villi exposed. The epithelial layer of the tissue fragment was then scraped off using a scalpel. The same scraping procedure was repeated several times in all four possible angles by stabilizing the tissue fragment consecutively from each of its four corners. The flattened and epithelial free remaining tissue, mostly comprised of muscularis externa was washed through serial passaging from 3 culture dishes containing PBS+GA and finally placed on a membrane where it stretched with sterile forceps. Finally, the membrane was placed in a 12-well plate and 1 ml of high glucose DMEM medium containing 10% FBS, gentamycin and amphotericin B (50 μg/ml and 2.5 μg/ml final concentrations, respectively) and incubated at 37° C. and 5% $CO_2$ atmosphere. Medium was changed daily. The tissue and medium were observed daily under optical microscope for contamination. The faithful implementation of the protocol yields flat muscularis externa tissue fragments devoid of bacterial, fungal or any other contamination.

In preparation for laser ablation/removal and/or LIFT printing, murine intestine was incubated at 37° C., 5% CO2, 100% relative humidity in media prior to LIFT printing. The mouse intestine (isolated from any region of the small or large intestine), spanning a rectangular area was cut at smaller pieces of ~6 mm, then removed from media and stretched on polycarbonate membranes (pore size 2 μm). In case the donor mouse is not sacrificed, the intestine is anastomosed. Excess media was removed prior to cell printing. Following the printing procedure, the mouse intestine was incubated at 37° C., 5% CO2, 100% relative humidity to initialize cell attachments to the tissue. Tissues were cultured for up to ten days.

EXAMPLE 5

Technique for Printing Murine Urothelial Cells onto Ablated Murine Intestinal Epithelium via Laser Induced Forward Transfer (LIFT)

The donor substrate 320 is coated underneath with a thin laser absorbing layer and a layer of the cell suspension material to be transferred. As the laser beam exits the laser source, it is guided through an optical setup, a configuration of optics and lenses, before being focused at the interface between the donor substrate 320 and the material to be transferred. The laser absorbing layer 335 is used to absorb the laser energy. When the laser beam is absorbed from the laser absorbing layer 335, a high-pressure vapor bubble, expanding rapidly, is created at the interface between the laser absorbing layer 335 and the cell suspension material due to rapid localized heating. The expansion of the bubble then helps eject the supernatant material from the donor substrate 320 towards the receiver substrate 160. Note that in our experiment, the receiver substrate 160 is mouse intestine.

Figure 11:
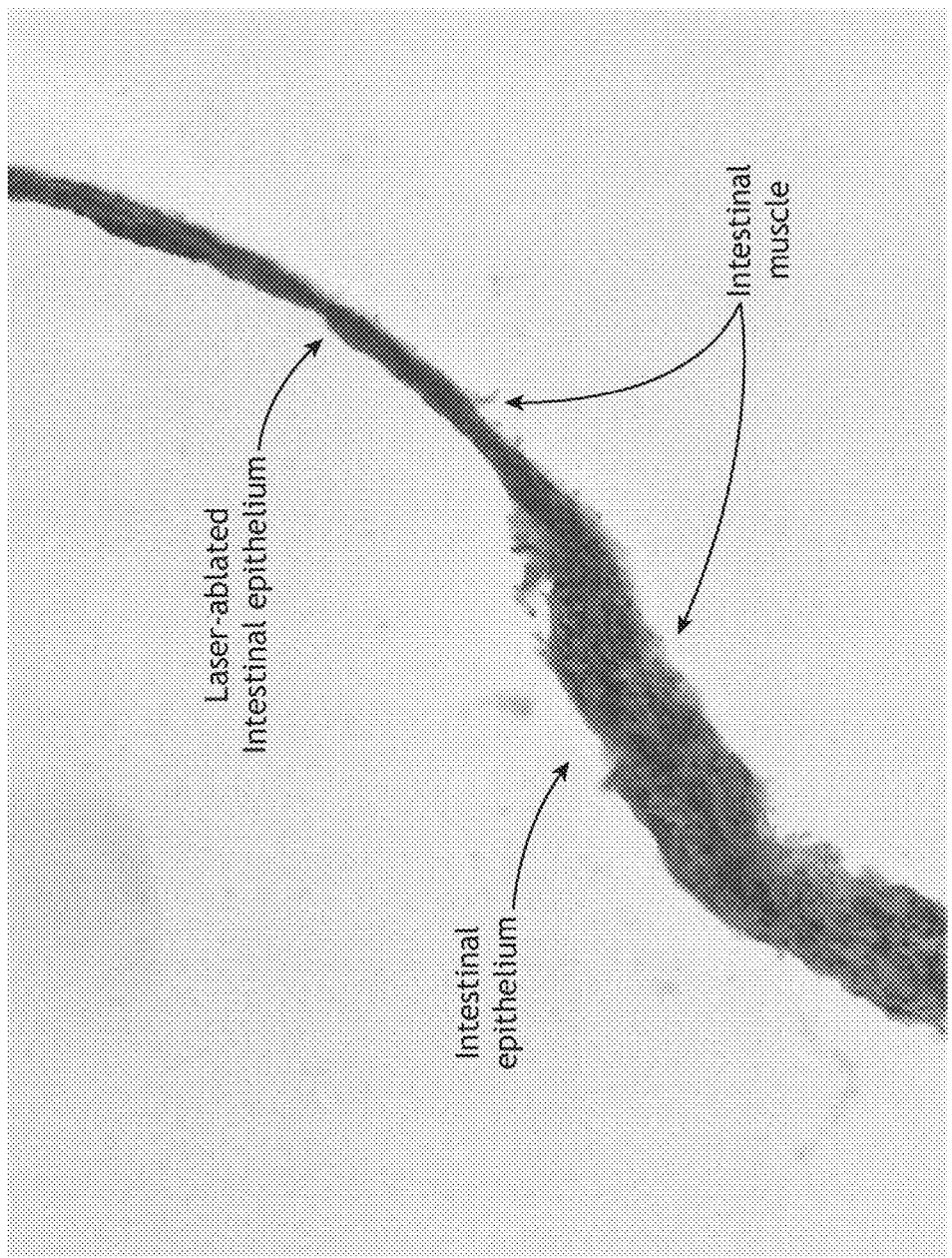
FIG. 11 is a micrograph illustrating the partial ablation of murine intestinal epithelium tissue via LIFT, in accordance with one or more embodiments of the disclosure.

The automated computer-aided stage setup allows the accurate transfer of a wide variety of patterns with a maximum speed of 10 mm/s. In our experiments, the printing speed that was used is 1 mm/s. Both the donor substrate 320 and the receiver substrate 160, are placed in parallel onto a holder stage, which can be moved in relation to the laser beams by using x-y-z translation stages (1 μm positioning resolution, 25 mm×25 mm travel range). The camera of the imaging system is coupled with a magnifying system, resulting in a total optical magnification of 5×. The laser is synchronized with the translation stages using an in-house software developed on LabVIEW FIG. 11 is a micrograph illustrating the partial ablation of murine intestinal epithelium tissue via LIFT, in accordance with one or more embodiments of the disclosure. The laser source employed is a Diode Pumped Solid State (STANDA STA-01SH-5, Lithuania) with 532 nm wavelength, 600 ps pulse duration and 1 kHz repetition rate. The laser pulses are focused with a 75 mm achromatic lens, producing an ablation/removal spot size of 40 μm in diameter. As shown in FIG. 11, the lower-half of the intestinal epithelium tissue is not ablated, and contains both an epithelium cell layer and an intestinal muscle layer. The top-half of the intestinal epithelium tissue has undergone ablation, resulting in the removal of the epithelial cells and retention of the intestinal muscle layer.

All LIFT experiments are performed at laser fluences between 100 and 500 $mJ/cm^2$, while the energy of the projected laser beam is controlled via an attenuator plate.

LIFT printing of the cell suspension is performed at 10 Hz repetition rate. The gap between the donor substrate 320 and the receiver substrate 160 can be adjusted and is set to a value in the range of 100 to 2000 μm, while the resulted printed droplet diameter is in the range of 50 to 200 μm. The achieved droplet size of the transferred cell suspension material can be effectively controlled by crucial LIFT printing conditions, such as the laser pulse energy (calculated by dividing the average power with the laser repetition rate), the distance between donor substrate 320 and the receiver substrate 160, the focused laser spot size, as well as the thickness of the energy absorbing layer and the cell suspension layer.

EXAMPLE 5

Results of LIFT Printed Cells in Ex Vivo Culture

Figure 12:
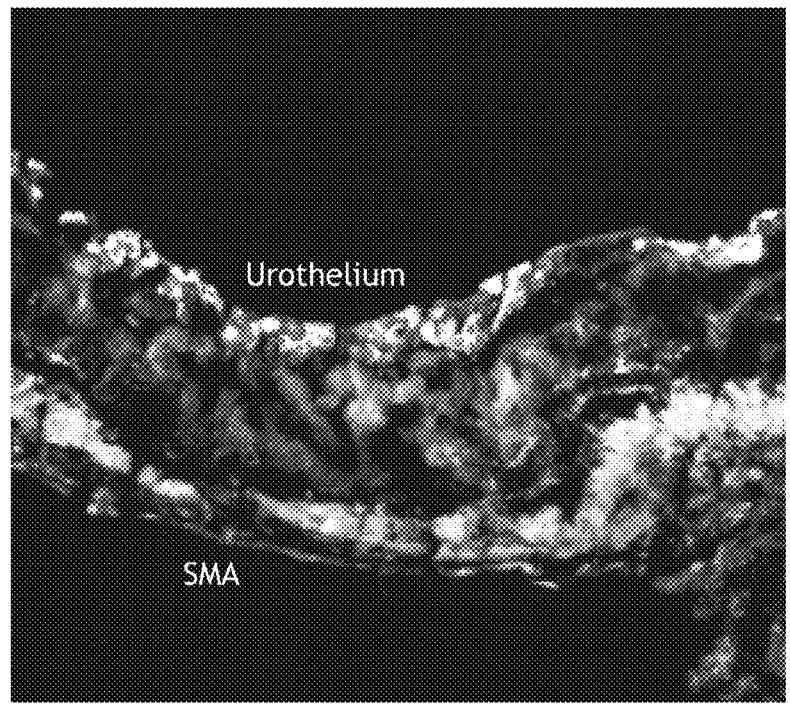
FIG. 12 illustrates a section of murine intestinal tissue printed with murine urothelial cells, in accordance with one or more embodiments of the disclosure, in accordance with one or more embodiments of the disclosure.

Following printing, the intestinal muscle tissue was grown in culture in appropriate media for up to 3 weeks. FIG. 12 illustrates a section of murine intestinal tissue printed with tdTomato-expressing murine urothelial cells (e.g., creating a urothelium) and grown in culture for two weeks, then assayed for tdTomato fluorescence and fluorescent immunostaining of smooth muscle actin, in accordance with one or more embodiments of the disclosure. The appearance of the both the tdTomato fluorescence from the urothelial cells (e.g., white patches along the urothelium) and the smooth muscle actin (SMA) immunofluorescence (e.g., white patches along the muscle layer, below the urothelium) from the intestinal cells suggest that the urothelial cells grew well covering the muscle surface and forming multilayer urothelium-like structures.

Figure 13:
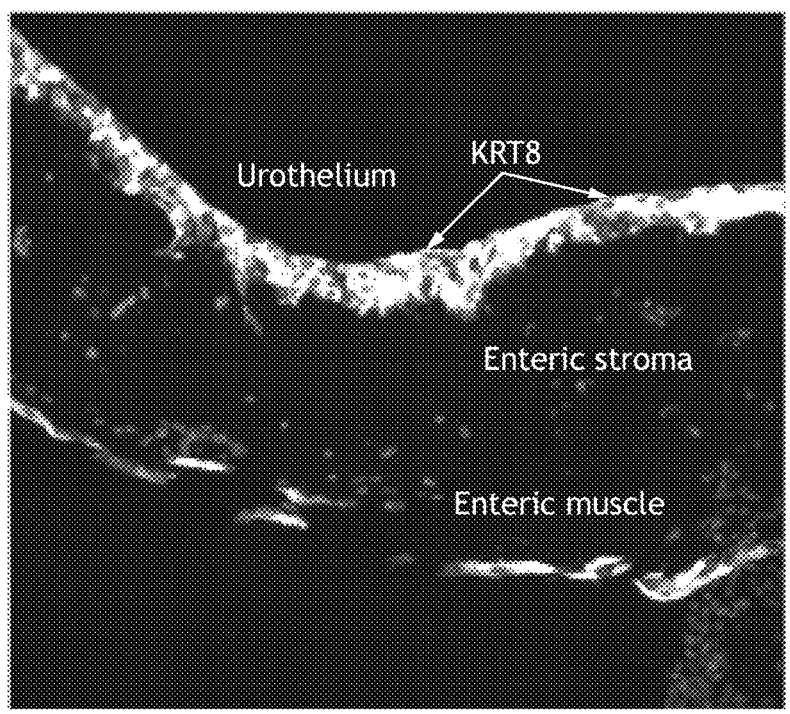
FIG. 13 is a micrograph illustrating a section of murine intestinal tissue printed with murine urothelial cells and grown in culture for two weeks in accordance with one or more embodiments of the disclosure.

FIG. 13 is a micrograph illustrating a section of murine intestinal tissue printed with tdTomato-expressing murine urothelial cells structures. (e.g., creating a urothelium) and grown in culture for two weeks, then assayed for tdTomato fluorescence (e.g., white patches along the urothelium) and KRT8. Immunofluorescence with antibodies against the differentiation marker cytokeratin 8 (KRT8) determined that several cells within the urothelium had differentiated into umbrella cells, indicating that after two weeks in culture, the multilayered urothelial structures begin to stratify, mimicking the normal urothelium.

Figure 14:
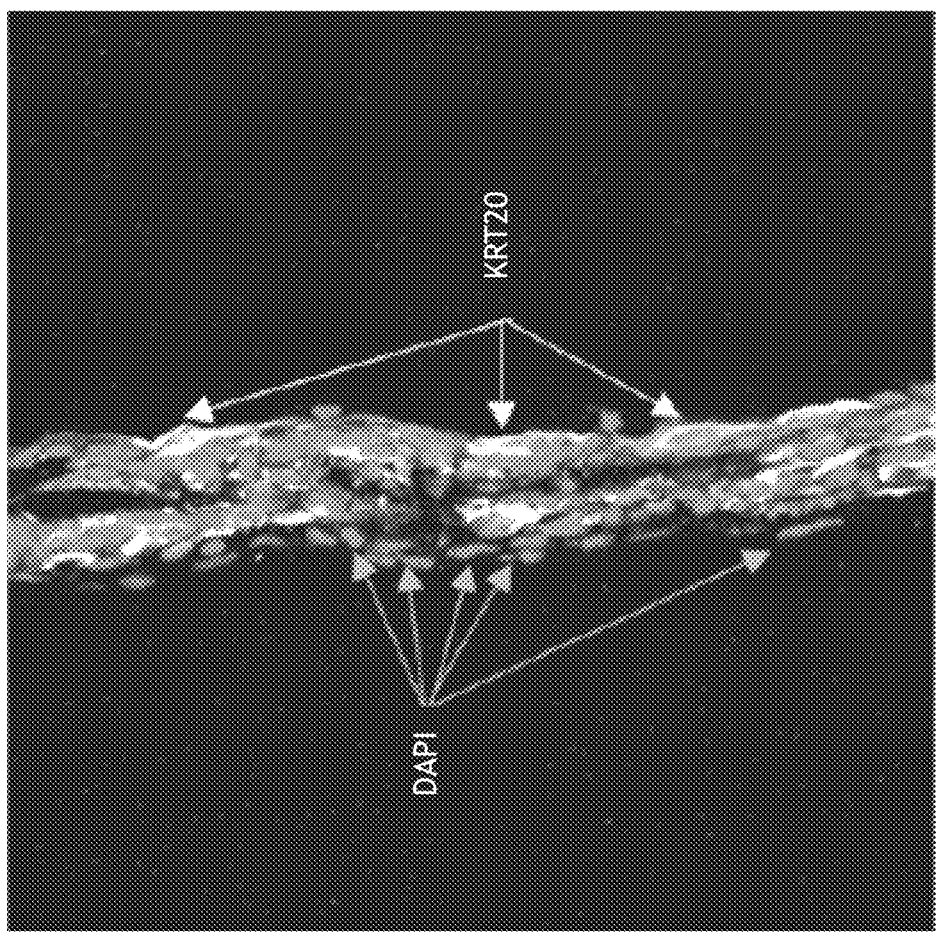
FIG. 14 is a micrograph illustrating murine urothelial cells printed onto denuded/ablated murine intestinal smooth muscle, in accordance with one or more embodiments of the disclosure.

FIG. 14 is a micrograph illustrating murine urothelial cells printed onto denuded/ablated murine intestinal smooth muscle, in accordance with one or more embodiments of the disclosure. The modified tissue was then grown in culture for two weeks, then assayed for the differentiated umbrella cell marker Cytokeratin-20 (KRT (20) via immunofluorescence, shown with white staining. Umbrella cells are crucial for urine:blood barrier formation in the bladder. The fluorescent stain DAPI (e.g., grey staining) was used as a nuclear counterstain. As shown in FIG. 14, the printed undifferentiated urothelial cells have adhered to and incorporated into the denuded smooth muscle, and have started differentiating into umbrella cells.

Figure 15:
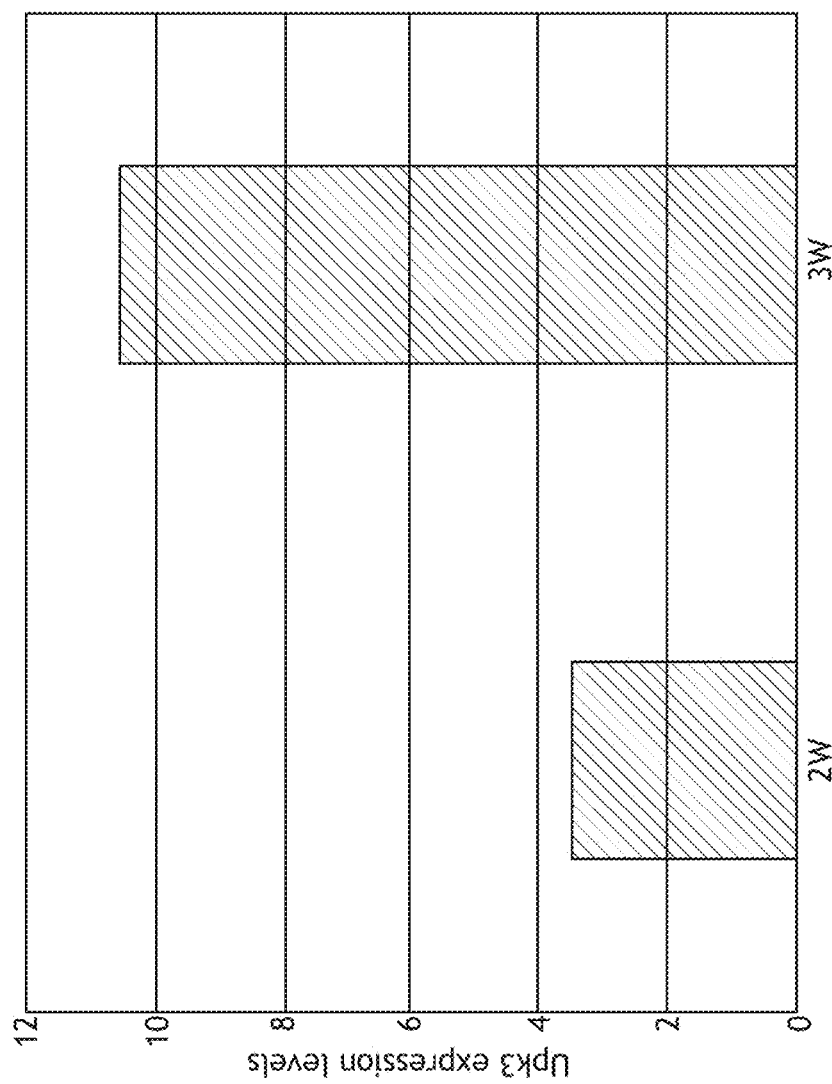
FIG. 15 is a graph illustrating the relative expression of the differentiation marker Upk3 in murine intestinal tissue printed with urothelial cells, in accordance with one or more embodiments of the disclosure.

FIG. 15 is a graph illustrating the relative expression of the differentiation marker Upk3 in murine intestinal tissue printed with urothelial cells and grown in culture for two and three weeks. Quantitative reverse transcription-polymerase chain reaction (qRT-PCR) analysis has indicated that after 2 weeks in culture, printed epithelial cells growing on muscle tissue express uroplakin-3 (Upk3), a terminal differentiation urothelial marker expressed by the umbrella layer of the urothelium. This implies that the printed composite tissue shows, at the molecular level, characteristic of fully functional urothelium.

EXAMPLE 6

Denudation/Ablation of Esophageal Tissue and Subsequent Printing of Keratinocytes via LIFT Patients with gastroesophageal reflux disease (GERD) and other esophageal conditions often develop dysplasias or cancers within the esophagus. These diseases and subsequent treatments may result in damage of the mucosal lining, and the loss of esophageal keratinocytes within the mucosal lining. In this Example, murine esophageal tissue has been isolated, denuded/ablated, and seeded with isolated primary murine esophageal keratinocytes in an effort to develop a method for treating esophageal keratinocyte loss. Protocols and results relating to Example 6 are detailed below.

Murine esophageal keratinocytes were isolated according to a method detailed in the manuscript "Isolation and characterization of mouse and human esophageal epithelial cells in 3D organotypic culture" published in *Nature Protocols* by Kalabis et al., on Jan. 12, 2012, which has been incorporated by reference in its entirety. Briefly, 2-month-old mice were euthanized and their esophagi were isolated in Petri dish containing Hanks' Balanced Salt Solution without Ca and Mg (HBSS-). They were washed in HBSS- and then cut open longitudinally with scissors. Up to ten collected esophagi were placed in 1 ml Dispase I solution (1 U/ml in HBSS-). After a short incubation at 37° C. for 10 min in a water bath, the epithelial sheet was peeled off each submucosa using forceps and placed in 1 ml Trypsin-EDTA solution (0.05% Trypsin-EDTA in HBSS-). The pooled epithelia were incubated at 370 C for 10 min, followed by vortex for 10 s. Vortexing enables the release of primary esophageal keratinocytes into the suspension which was then placed in 8 ml of HBSS- supplemented with 5% FBS to inactivate trypsin. The remaining epithelia were incubated in a fresh 1 ml trypsin solution and added to the first pooled epithelia. The now separated and pooled keratinocytes were filtered through a 40 µm cell strained, and collected through centrifugation (188×g for 5 min). The cell pellet was finally resuspended in the appropriate volume of KSFM (keratinocyte serum free medium with 0.018 mM Ca, supplemented with bovine pituitary extract, EGF, gentamycin and nystatin) and kept on ice until printed. This method may also be used to isolate genetically modified primary cells from mouse strains having fluorescently labeled esophageal keratinocytes.

For isolation and de-epithelialization of esophageal tissues, esophagi were harvested from adult mice (e.g., 2-month-old mice). After euthanasia, esophagi were harvested and placed in HBSS-. In some experiments the whole esophageal epithelium was removed by peeling it off from submucosa using forceps. In some others, partial sections of the tissue were de-epithelialized. In those cases, esophagi were cut open longitudinally and one side was stably immobilized in a plastic surface with two micro pins at its one edge while the epithelial side faced up. The tissue was then stretched and in 1 cm from the edge it was pinned and cut across with a scalpel under a stereoscope. While stretched, a small section of the epithelium near the middle of the 1 cm long sample was removed by uplifting the epithelial sheet on one side and cut across with micro-scissors. Similarly, a parallel cross section was conducted about 2 mm apart from the first. Then using forceps, this 2 mm-thick epithelial sheet was removed from the immobilized esophageal section. The remaining esophageal sample was processed similarly to yield 2-3 samples. Printing of isolated murine esophageal keratinocytes onto the de-epithelialized esophageal tissues was performed similarly as the printing of urothelial cells as detailed herein.

In both partial and complete de-epithelialized samples, the tissue sections were placed on top of a Cyclopore track etched membrane and immobilized in a ring shape plastic base with 4 pins at their edges. This 3 mm tall ring base enables the horizontal placement of the sample within a well of a 12-well culture plate with 1 ml of KSFM medium and its growth at the air-liquid interface. The stitched samples are also utilized as receiver substrate in printing experiments.

The seeding of denuded esophageal tissue may be used to treat damaged esophageal tissues, where the esophageal mucosa has been damaged via fibrosis or removed via endoscopic resection, photodynamic therapy, radiofrequency ablation, and the like. In cases where esophageal tissue is not available for seeding (e.g., following esophagectomy), other tissues may be used as the base tissue for seeding keratinocytes (e.g., esophageal or other) including but not limited to stomach tissue, large intestinal tissue (e.g., from left colon or right colon), and small intestine (e.g., the jejunum).

EXAMPLE 7

Denudation/Ablation of Esophageal Tissue and Subsequent Printing of Keratinocytes via LIFT FIG. 16A-D are immunofluorescence micrographs illustrating the printing of isolated esophageal keratinocytes onto denuded intestinal smooth muscle, in accordance with one or more embodiments of the disclosure. The esophageal keratinocytes were isolated via the method described in Example 6. The preparation of the denuded intestinal smooth muscle, and the printing of esophageal keratinocytes onto the denuded intestinal smooth muscle were performed as detailed herein.

Figure 16B:
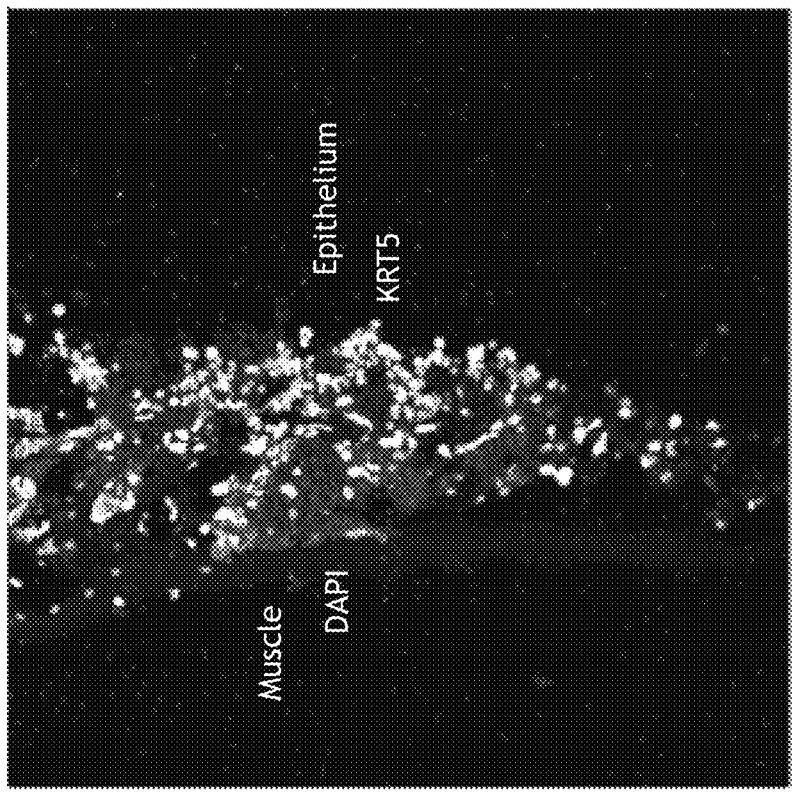
FIG. 16A-B are immunofluorescence micrographs illustrating the printing of isolated esophageal keratinocytes onto denuded intestinal smooth muscle, in accordance with one or more embodiments of the disclosure.
Figure 16A:
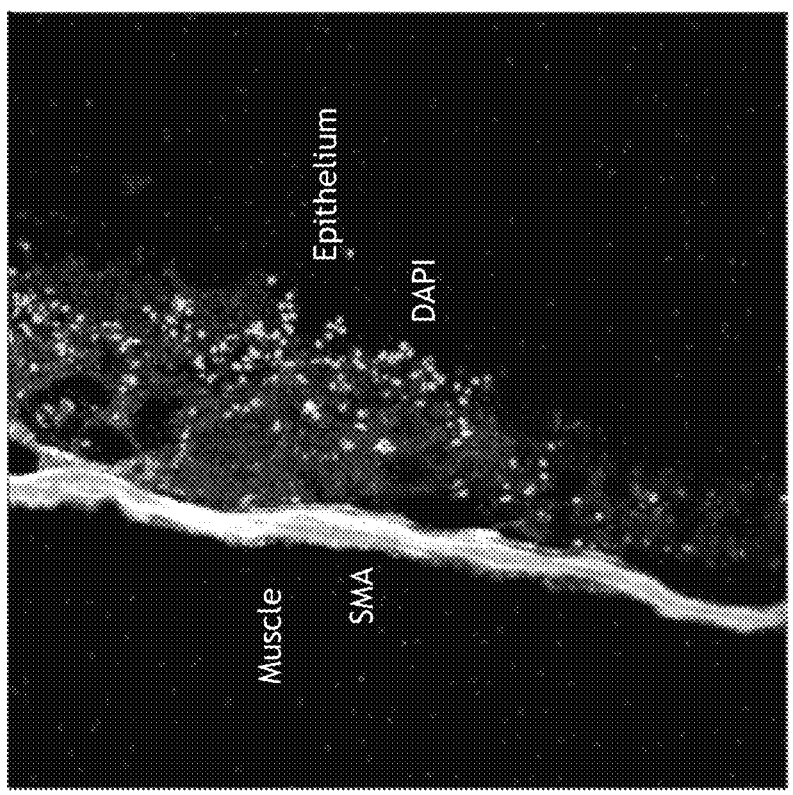

Referring to FIG. 16A, the denuded intestinal smooth muscle is stained with antibodies recognizing smooth muscle actin (SMA), resulting in a bright and well-defined vertical stripe. In contrast, the printed primary esophageal keratinocytes can be visualized as dark-grey appearing DAPI-stained cells with speckled or no SMA staining along the epithelium. Referring to FIG. 16B, the printed primary esophageal keratinocytes are stained with KRT5 antibodies and present as bright speckles. In contrast, the intestinal smooth muscle cells are visualized as dark-grey DAPI-stained cells with no KRT5 staining. These results show the incorporation of printed esophageal keratinocytes into denuded intestinal smooth muscle.

Figures 16C, 16D:
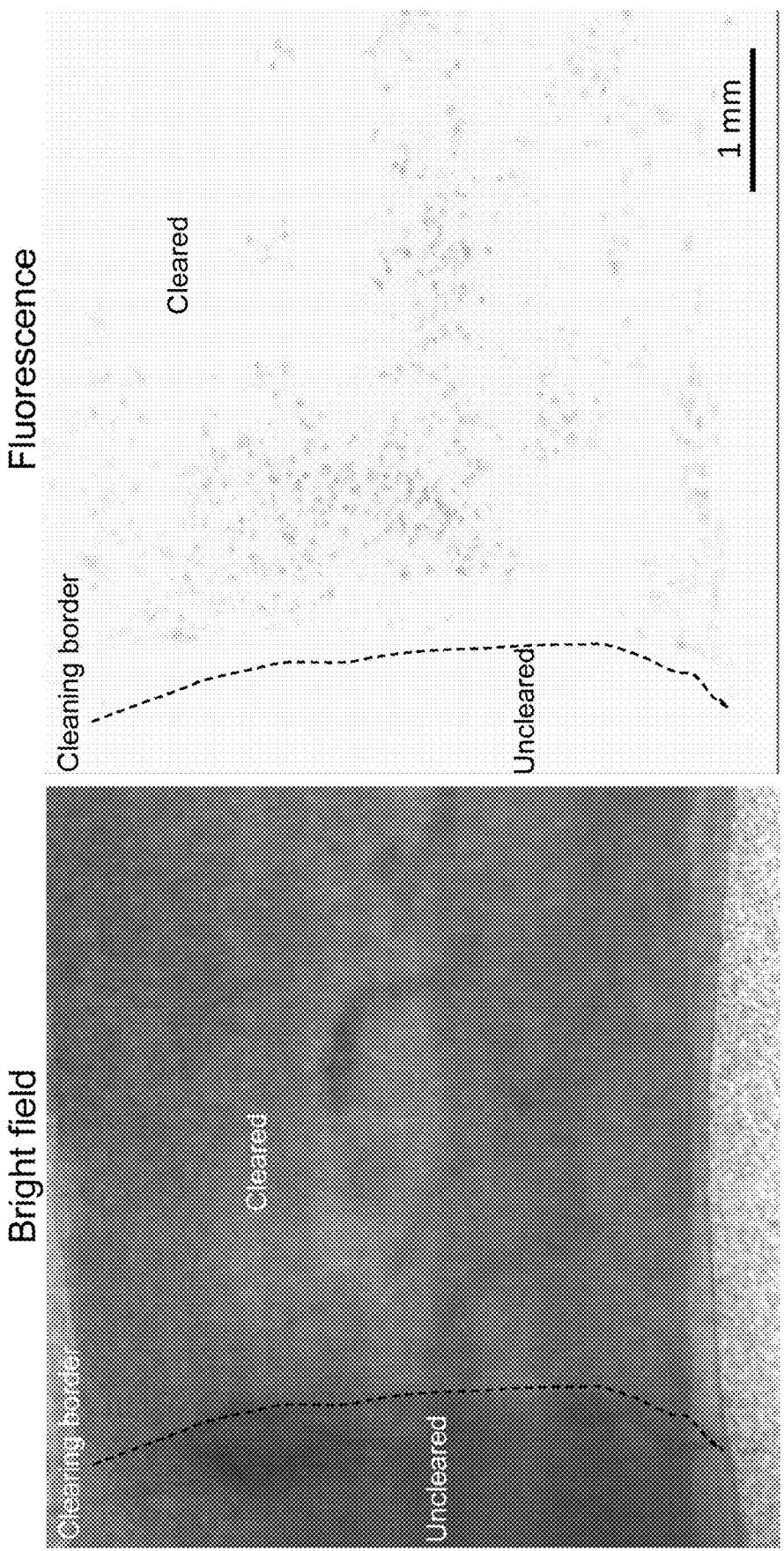
FIG. 16C-D are immunofluorescence micrographs illustrating the integration of printed tdTomato-labeled esophageal keratinocytes on a denuded segment, in accordance with one or more embodiments of the disclosure.

Referring to FIG. 16C, a section of a murine esophagus is shown with a denuded (e.g., cleared) area, as well as an uncleared area, with a dotted line demarking a border between the cleared and uncleared areas. Referring to section 16D, the cleared section in 16C was printed with murine esophageal keratinocytes sourced from a transgenic mouse having a tdTomato transgene, and photographed via fluorescent microscopy after three days. The fluorescent tdTomato-labeled esophageal cells are shown having a speckled appearance upon the cleared area of the esophagus section.

EXAMPLE 8

Isolation of Cartilaginous Tissue and Primary Murine Costal Chondrocytes, with Subsequent Printing of Primary Murine Costal Chondrocytes via LIFT Tissue printed with healthy cartilage cells may be used to treat a variety of arthritic conditions within the body, such as osteoarthritis, and prevent further arthritic damage from inflammatory diseases known to accelerate arthritis. In this example, chondrocytes from neonatal mice were isolated and printed onto a cartilage tissue (e.g., from sterna and/or ribs) of another mouse.

Primary chondrocytes were isolated according to a method detailed in the manuscript "Primary Murine Growth Plate and Articular Chondrocyte Isolation and Cell Culture" published in Osteoporosis and Osteoarthritis by Jonason et al., on Sep. 17, 2014, which has been incorporated by reference in its entirety. In brief, early postnatal pups (2-4 days) euthanized and washed in 70% ethanol before placing them in a sterile culture dish with 10 ml of phosphate buffer saline (PBS) placed on ice. Using sterile scissors and forceps, the anterior rib cage and sternum was isolated en bloc and transferred to a 50 ml conical tube on ice.

Upon harvest completion, the tissues were transferred in 15 ml conical tube containing 10 ml Pronase solution (2 mg/ml). The tube was then incubated at 37° C. for 60 min in a shaking (80 rpm) water bath. Three washes with 50 ml PBS followed the pronase incubation where the tube was swirled aggressively in order to detach the remaining soft tissue. The cages were then transferred in 10 ml of 3 mg/ml Collagenase D solution for 90 min in cell culture incubator with the lid loosened. After at least 3 PBS washes as above, the soft tissue anterior rib cages were incubated in a culture dish containing 10 ml of 3 mg/ml Collagenase D solution in a culture incubator for 3-5 h. This final Collagenase D treatment will release the costal chondrocytes into the solution and will digest all chondral tissues progressively. Swirling the dish and up and down pipetting every hour encourages the digestion process. Since the duration of this step varies, examination under the microscope every hour was performed to avoid overdigestion. Upon completion of tissue digestion, the solution was passed through 70 μm cell strainer and the cells were collected via centrifugation (1500 rpm for 5 min). Finally, the cells were washed once in DMEM medium supplemented with 10% non-heat inactivated FBS and 100 U penicillin/streptomycin and after centrifugation were resuspended in the desired volume of medium and kept on ice until printed. The same process was followed to isolate genetically modified primary cells from mouse strains that their chondrocytes are fluorescently labeled.

Receiver cartilage tissues were processed in a manner similar to that described herein, with anterior rib cages and sternum isolated from donor mice. The donor mice may be of variable age, but the chondral tissue of the ribs and sternum is replaced by bone over time. Newborns are the richest in cartilage while adult mice have only the xiphoid cartilage made of chondral tissue. However, this sternum part is covered in several layers of soft tissue and fat. In order to expose xiphoid for bioprinting experiments, all covering tissues were carefully removed manually with forceps in culture plates with PBS under the stereoscope. The ribs are usually preserved during the clearing process in order to enable the stability of the specimen in the solution. Once the xiphoid cartilage is cleared, the rest of the anterior rib cage is excised with a scalpel near the xiphoid junction. Xiphoid tissues preserved in typical DMEM medium for several days in culture incubator (humidified atmosphere of 5% CO2 at 370 C). Printing of the isolated primary chondrocytes onto the isolated receiver cartilage tissue via LIFT was performed as described herein.

Figure 17:
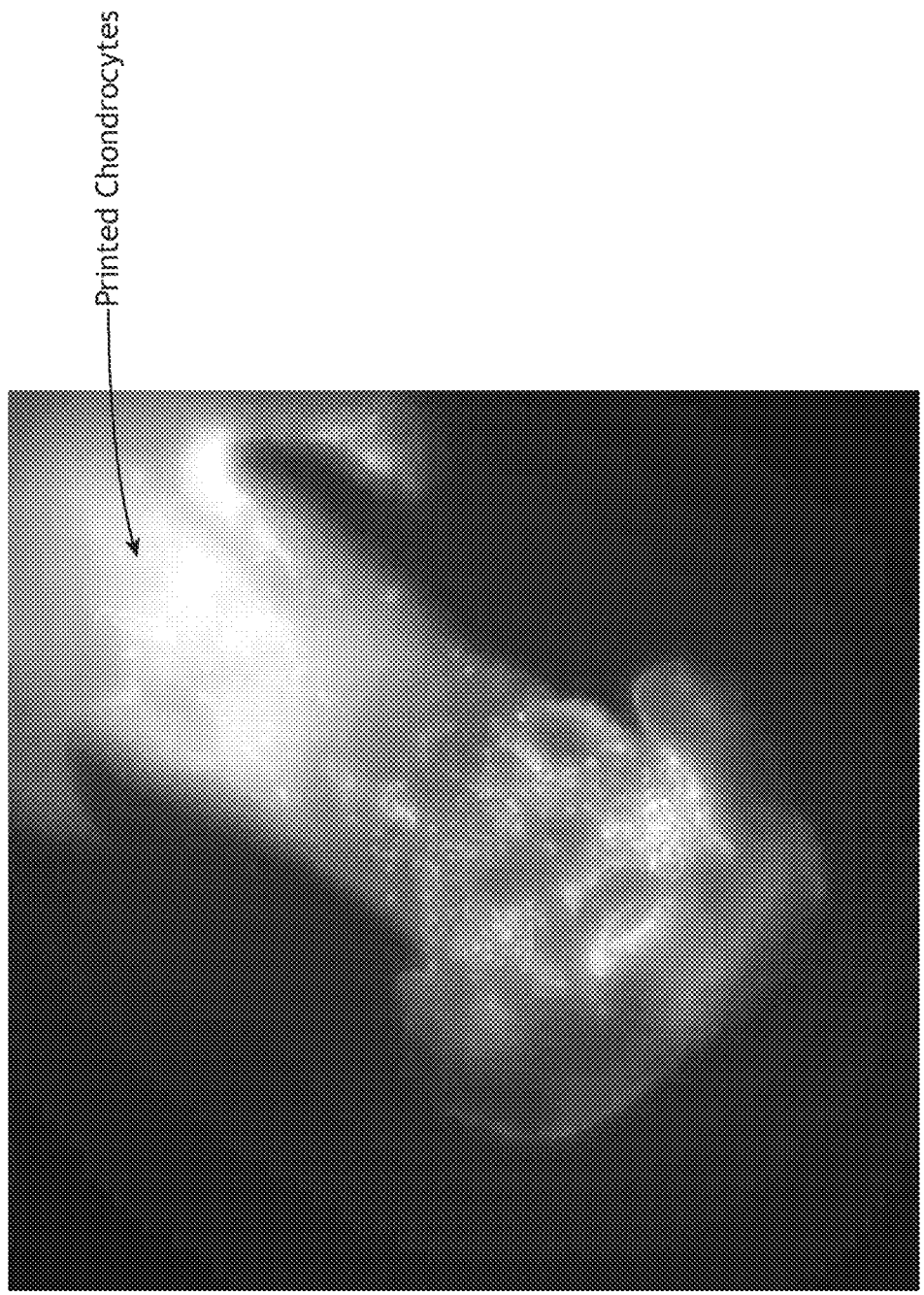
FIG. 17 is an immunofluorescence micrograph illustrating the staining of printed primary chondrocytes onto a sternum of a three-day old donor mouse, in accordance with one or more embodiments of the disclosure.

FIG. 17 is an immunofluorescence micrograph illustrating the staining of printed primary chondrocytes onto a sternum of a three-day old donor mouse, in accordance with one or more embodiments of the disclosure. The primary chondrocytes were isolated from three-day old mice, and were treated with the dye, Hoechst 33258, prior to printing. The primary chondrocytes were printed on the two edges of the sternum. The immunofluorescence micrograph was taken 24 hours after printing. The mouse sternum readily fluoresces due to the presence of primary chondrocytes labeled with the Hoechst 33258 dye, confirming the ability of chondrocytes to be printed onto cartilage tissue via lift.

EXAMPLE 9

Isolation of Murine Intestinal or Colonic Segments and their Epithelial Denudation via Chemical-Mechanical Means Chemical-Mechanical means for isolating murine intestinal or colonic segments may be performed similar to methods detailed in the manuscript "Separation of Intact Intestinal Epithelium from Mesenchyme" published in *Biotechniques* by Nik and Carlsson in July, 2014, which has been incorporated by reference in its entirety. Desired intestinal or colonic parts (jejunum or mid and distal colon, respectively) were excised aseptically from 1.5-2 months old mice after euthanasia. The tubular tissues were washed several times with saline or sterile PBS delivered through a syringe under aseptic conditions. Tissues were then completely inverted to expose the epithelium and cut in sections of 4-5 cm. A stitch was used to close one end of the tubular tissue and a gavage needle was stitched on the other end. Through a syringe, the tissue was blown with air and baptized in ice cold recovery solution for 20 min. Every 5 min the air was blown out and in again to mechanically push the epithelial crypts to detach from basal membrane. After the incubation, the tissue was transferred in ice cold PBS and swirled to liberate the tissue from its epithelium. Next, the submucosal parts were cut longitudinally and then vertically at 1 cm intervals. The produced segments were finally placed on top of a Cyclospora track-etched membrane and immobilized in a ring shape plastic base with 4 pins at their edges, as above. The 3 mm tall ring base enables the horizontal placement of the sample within a well of a 12-well culture plate with 1 m of typical DMEM medium supplemented with antibiotic cocktail (Gentamysin, Ampotericin and Cypro) and its growth at the air-liquid interface. The stitched samples were then utilized as receiver substrate in printing experiments.

Those skilled in the art will recognize that a wide variety of modifications, alterations, and combinations can be made with respect to the above-described embodiments without departing from the spirit and scope of the invention, and that such modifications, alterations, and combinations are to be viewed as being within the ambit of the inventive concept.

The previous description is presented to enable one of ordinary skill in the art to make and use the invention as provided in the context of a particular application and its requirements. Various modifications to the described embodiments will be apparent to those with skill in the art, and the general principles defined herein may be applied to other embodiments. Additionally, phrases that disclose the addition of one component to another component are not limiting to the sequence or placement of one component to another component. For example, the addition of component A to component B may have the same meaning as the addition of component B to component A (e.g., the two components are mixed together). Therefore, the present invention is not intended to be limited to the particular embodiments shown and described, but is to be accorded the widest scope consistent with the principles and novel features herein disclosed.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

It is further contemplated that each of the embodiments of the method described above may include any other step(s) of any other method(s) described herein. In addition, each of the embodiments of the method described above may be performed by any of the systems described herein.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly interactable and/or wirelessly interacting components and/or logically interacting and/or logically interactable components.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, and the like" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed:

1. A method comprising:
   generating a receiver substrate, wherein the receiver substrate comprises intestinal tissue;
   removing a portion of the receiver substrate via one or more lasers to expose a target layer of the receiver substrate for placement of donor material, wherein the donor material includes one or more cells suitable for proliferation on the target layer, wherein the donor material further comprises urothelial cells, wherein:
      the urothelial cells comprise at least one of differentiated induced pluripotent stem cells (iPS) or stem cells of mesodermal or endodermal origin, or
      the urothelial cells are derived from at least one of a bladder, a ureter, a urethra, or a renal pelvis;
   generating a donor substrate, wherein the donor substrate comprises a back surface and a front surface;
   applying a coating to the front surface, wherein the coating includes donor material;
   aligning the front surface of the donor substrate to be parallel to and facing the receiver substrate, wherein the donor material is disposed adjacent to the target layer; and
   irradiating the coating through the back surface of the donor substrate with one or more laser pulses produced by a second laser to transfer a portion of the donor material to the target layer, and
   proliferating the one or more cells of the donor material on the target material to form a transplantable tissue.

2. The method of claim 1, further comprising:
   scanning the donor substrate through a focal point of the one or more laser pulses while irradiating the donor material with the one or more laser pulses to continuously provide new donor material to transfer to the receiver substrate; and
   scanning the receiver substrate while irradiating the donor material with the one or more laser pulses to form a selected pattern of the donor material on the target layer.

3. The method of claim 2, wherein the selected pattern of the donor material on the target layer comprises:
   a layer of the donor material on the target layer.

4. The method of claim 1, wherein removing the portion of the receiver substrate via the one or more lasers to expose the target layer of the receiver substrate comprises:
   removing one or more crypt cells from the intestinal tissue without removing a stromal layer or a muscle layer from the intestinal tissue.

5. The method of claim 1, wherein removing the portion of the receiver substrate via the one or more lasers to expose the target layer of the receiver substrate comprises:
   denuding at least a portion of an epithelial layer of the intestinal tissue without removing a stromal layer or a muscle layer from the intestinal tissue.

6. The method of claim 1, wherein the donor material comprises at least one of a tissue, a protein, a nucleic acid, an extracellular material, a scaffolding material, an epithelial cell, a urothelial cell, a fibroblast, a mesenchymal cell, an adipocyte, an immune cell, a muscle cell, a nerve cell, an insulinogenic cell, a keratinocyte, a chondrocyte or a stem cell.

7. The method of claim 1, wherein the receiver substrate comprises at least one of an extracellular matrix, intestinal tissue, bladder tissue, stomach tissue, cartilaginous tissue, esophageal tissue, a cell-containing tissue, an organ, a portion of an organ, or an organoid.

8. The method of claim 1, wherein the applying the coating comprises:
   applying a dynamic release layer to the front surface of the donor substrate; and
   applying the donor material to the dynamic release layer.

9. The method of claim 1, wherein the removing a portion of the receiver substrate removes at least one of a layer of cells, an intestinal crypt, an extracellular matrix, a tissue, or portion of an organ from the receiver substrate.

10. A method comprising:
    generating a receiver substrate, wherein the receiver substrate comprises biological tissue;
    removing a portion of the receiver substrate via one or more lasers to expose a target layer of the receiver substrate for placement of donor material, wherein the donor material includes one or more cells suitable for proliferation on the target layer, wherein removing the portion of the receiver substrate via the one or more lasers to expose the target layer of the receiver substrate comprises:
       removing one or more crypt cells from the intestinal tissue without removing a stromal layer or a muscle layer from the intestinal tissue or
       or denuding at least a portion of an epithelial layer of the intestinal tissue without removing a stromal layer or a muscle layer from the intestinal tissue;
    generating a donor substrate, wherein the donor substrate comprises a back surface and a front surface;
    applying a coating to the front surface, wherein the coating includes donor material;
    aligning the front surface of the donor substrate to be parallel to and facing the receiver substrate, wherein the donor material is disposed adjacent to the target layer; and
    irradiating the coating through the back surface of the donor substrate with one or more laser pulses produced by a second laser to transfer a portion of the donor material to the target layer;
    scanning the donor substrate through a focal point of the second laser while irradiating the donor material with the second laser to continuously provide new donor material to transfer to the receiver substrate; and
    scanning the receiver substrate while irradiating the donor material with the second laser to form a selected pattern of the donor material on the target layer.

11. The method of claim 10, wherein the receiver substrate comprises at least one of an extracellular matrix, intestinal tissue, bladder tissue, stomach tissue, cartilaginous tissue, esophageal tissue, a cell-containing tissue, an organ, a portion of an organ, or an organoid, wherein the donor material comprises at least one of a tissue, a protein, a nucleic acid, an extracellular material, a scaffolding material, an epithelial cell, a urothelial cell, a fibroblast, a mesenchymal cell, an adipocyte, an immune cell, a muscle cell, a nerve cell, an insulinogenic cell, a keratinocyte, a chondrocyte or a stem cell.

* * * * *